(12) United States Patent
Persson et al.

(10) Patent No.: US 6,180,625 B1
(45) Date of Patent: Jan. 30, 2001

(54) HETEROCYCLIC COMPOUNDS REGULATING CLOTTING

(75) Inventors: Egon Persson, Malmø (SE); Palle Jakobsen, Værløse; Helle Worsaae, Gentofte, both of (DK)

(73) Assignee: Novo Nordisk A/S, Bagsvaerd (DK)

(*) Notice: Under 35 U.S.C. 154(b), the term of this patent shall be extended for 0 days.

(21) Appl. No.: 09/274,448

(22) Filed: Mar. 22, 1999

Related U.S. Application Data

(60) Provisional application No. 60/081,068, filed on Apr. 8, 1998, and provisional application No. 60/111,673, filed on Dec. 10, 1998.

(30) Foreign Application Priority Data

| Mar. 24, 1998 | (DK) | 0413/98 |
| Apr. 2, 1998 | (DK) | 0464/98 |
| Nov. 26, 1998 | (DK) | 1559/98 |

(51) Int. Cl.[7] .................... A61K 31/535; C07D 265/12
(52) U.S. Cl. ........................... 514/230.5; 544/92
(58) Field of Search ..................... 514/230.5; 544/92

(56) References Cited

U.S. PATENT DOCUMENTS 5,489,686  2/1996  Blankley et al. ............ 546/147

FOREIGN PATENT DOCUMENTS

| 0 147 211 | 7/1985 | (EP) . |
| 0 206 323 | 12/1986 | (EP) . |
| WO 91/19707 | 12/1991 | (WO) . |
| WO 96/07648 | 3/1996 | (WO) . |
| WO 97/49684 | 12/1997 | (WO) . |

OTHER PUBLICATIONS

Ulrich Rose, "2–Aryl–Substituted 4H–3, 1–Benzoxazin–4–ones as Novel Active Substances For The Cardiovascular System", Journal of Heterocyclic Chemistry, 28 (1991): 8, pp. 2005–2012.

*Primary Examiner*—Mukund J. Shah
*Assistant Examiner*—Tamthom N. Truong
(74) *Attorney, Agent, or Firm*—Steve T. Zelson, Esq.; Carol E. Rozek, Esq.

(57) ABSTRACT

Compounds of formula (I)

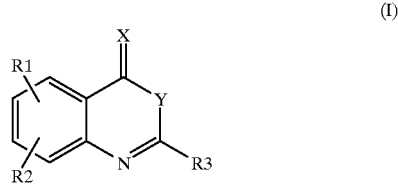

as factor VII-tissue factor inhibitors as well as novel benzoxazin derivatives are disclosed, wherein R1, R2, R3, X and Y are as defined in the specification. These compounds, and pharmaceutically acceptable salts thereof, have been shown to be inhibitors of factor VIIa-tissue factor activity and have anticoagulant properties. These compounds are useful for treating deficiencies of blood clotting factors or the effects of inhibitors to blood clotting factors. Methods for inhibiting clotting activity are also disclosed.

13 Claims, No Drawings

HETEROCYCLIC COMPOUNDS REGULATING CLOTTING

CROSS-REFERENCE TO RELATED APPLICATIONS

This application claims priority under 35 U.S.C. 119 of Danish application serial nos. 0413/98, 0464/98, and 1559/98 filed Mar. 24, 1998, Apr. 2, 1998 and Nov. 26, 1998, and U.S. Provisional Ser. Nos. 60/081,068 and 60/111,673 filed on Apr. 8, 1998 and Dec. 10, 1998, the contents of which are fully incorporated herein by reference.

FIELD OF INVENTION

The present invention relates to reagents useful as anticoagulants. More specifically, the invention relates to the use of compounds having the formula I, and pharmaceutical salts thereof, as anticoagulants. The compounds inhibit the ability of factor VIIa (fVIIa) in complex with tissue factor (TF) to cleave a low-molecular weight substrate and/or factor X and, as a result, blood coagulation initiated by tissue factor is inhibited. The invention further relates to the use of compound I as an inhibitor of clotting activity, and methods of inhibiting clotting activity, tissue factor activity, and FVIIa activity as well as methods for treatment of coagulation related diseases states.

The invention also relates to novel compounds with anticoagulative effect and pharmaceutical compositions comprising such compounds.

BACKGROUND OF INVENTION

Blood coagulation is a process consisting of a complex interaction of various blood components, or factors, which eventually gives rise to a fibrin clot. Generally, the blood components which participate in what has been referred to as the coagulation "cascade" are proenzymes or zymogens, enzymatically inactive proteins, which are converted to proteolytic enzymes by the action of an activator, itself an activated clotting factor. Coagulation factors that have undergone such a conversion and generally referred to as "active factors", and are designated by the addition of the letter "a" to the name of the coagulation factor (e.g. fVIIa).

Activated factor X (fXa) is required to convert prothrombin to thrombin, which then converts fibrinogen to fibrin as a final stage in forming a fibrin clot. There are two systems, or pathways that promote the activation of factor X. The "intrinsic pathway" refers to those reactions that lead to thrombin formation through utilisation of factors present only in plasma. A series of protease-mediated activations ultimately generates factor IXa, which, in conjunction with factor VIIIa, cleaves factor X into Xa. An identical proteolysis is effected by fVIIa and its cofactor TF in the "extrinsic pathway" of blood coagulation. TF is a membrane bound protein and does not normally circulate in plasma. Upon vessel disruption, however, it is exposed and forms a complex with fVIIa to catalyse factor X activation or factor IX activation in the presence of $Ca^{2+}$ and phospholipid (Nemerson and Gentry, *Biochemistry* 25:4020–4033 (1986)). While the relative importance of the two coagulation pathways in hemostasis is unclear, in recent years fVIIa and TF have been found to play a pivotal role in the initiation and regulation of blood coagulation.

FVII is a trace plasma glycoprotein that circulates in blood as a single-chain zymogen. The zymogen is catalytically inactive (Williams et al., *J. Biol. Chem.* 264:7536–7543 (1989); Rao et al., *Proc. Natl. Acad. Sci. USA.* 85:6687–6691 (1988)). Single-chain fVII may be converted to two-chain fVIIa by factor Xa, factor XIIa, factor IXa, fVIIa or thrombin in vitro. Factor Xa is believed to be the major physiological activator of fVII. Like several other plasma proteins involved in hemostasis, fVII is dependent on vitamin K for its activity, which is required for the gamma-carboxylation of multiple glutamic acid residues that are clustered in the amino terminus of the protein. These gamma-carboxylated glutamic acids are required for the metal-associated interaction of fVII with phospholipids.

The conversion of zymogen fVII into the activated two-chain molecule occurs by cleavage of an internal Arg152-Ile153 peptide bond (Hagen et al., *Proc. Natl. Acad. Sci. USA* 83: 2412–2416 (1986); Thim et al., *Biochemistry* 27:7785–7793 (1988)). In the presence of TF, phospholipids and calcium ions, the two-chain fVIIa rapidly activates factor X or factor IX by limited proteolysis.

It is often desirable to selectively block or inhibit the coagulation cascade in a patient. Anticoagulants such as heparin, coumarin, derivatives of coumarin, indandione derivatives, thrombin inhibitors, factor Xa inhibitors, modified fVII or other agents may be used.

Inhibition of coagulation is beneficial in a number of diseased states, for example 25 during kidney dialysis, or to treat deep vein thrombosis, disseminated intravascular coagulation (DIC) and a host of other medical disorders. For example, heparin treatment or extracorporeal treatment with citrate ions (U.S. Pat. No. 4,500,309) may be used in dialysis to prevent coagulation during the course of treatment. Heparin is also used in preventing deep vein thrombosis in patients undergoing surgery. Treatment with heparin and other anticoagulants may, however, have undesirable side effects. Available anticoagulants generally act throughout the body, rather than acting specifically at the site of injury, i.e. the site at which the coagulation cascade is active. Heparin, for example, may cause severe bleedings. Furthermore, with a half-life of approximately 80 minutes, heparin is rapidly cleared from the blood, necessitating frequent administrating. Because heparin acts as a cofactor for antithrombin III (AT III), and AT III is rapidly depleted in DIC treatment, it is often difficult to maintain the proper heparin dosage, necessitating continuous monitoring of AT III and heparin levels. Heparin is also ineffective if AT III depletion is extreme. Further, prolonged use of heparin may also increase platelet aggregation and reduce platelet count, and has been implicated in the development of osteoporosis. Indandione derivatives may also have toxic side effects.

Other known anticoagulants comprise thrombin and factor Xa inhibitors derived from bloodsucking organisms. Antithrombins, hirudin, hirulog and hirugen are recombinant proteins or peptides derived from the leach *Hirudo medicinalis*, whereas the factor Xa inhibitor antistatin and the recombinant derivative rTAP are tick-derived proteins. Inhibitors of platelet aggregation such as monoclonal antibodies or synthetic peptides, which interfere with the platelet receptor GPIIb/IIa are also effective as anticoagulants.

Bleeding complications are observed as an undesired major disadvantage of anti-thrombin, anti-factor Xa, as well as anti-platelet reagents. This side effect is strongly decreased or absent with inhibitors of the fVIIa/TF activity. Such anticoagulants comprise the physiological inhibitor TFPI (tissue factor pathway inhibitor) and modified fVII (fVIIai), which is fVIIa modified in such a way that it is catalytically inactive but still binds to TF and competes with active fVIIa.

In addition to the anticoagulants briefly described above, several naturally occurring proteins have been found to have anticoagulant activity. For example, Reutelingsperger (U.S. Pat. No. 4,736,018) isolated anticoagulant proteins from bovine aorta and human umbilical vein arteries. Maki et al. (U.S. Pat. No. 4,732,891) disclose human placenta-derived anticoagulant proteins. In addition, AT III has been proposed as a therapeutic anticoagulant (Schipper et al., Lancet 1 (8069): 854–856 (1978); Jordan, U.S. Pat. No. 4,386,025; Bock et al., U.S. Pat. No. 4,517,294).

Proliferation of smooth muscle cells (SMCs) in the vessel wall is an important event in the formation of vascular lesions in atherosclerosis, after vascular reconstruction or in response to other vascular injury. For example, treatment of atherosclerosis frequently includes the clearing of blocked vessels by angioplasty, endarterectomy or reduction atherectomy, or by bypass grafting, surgical procedures in which atherosclerotic plaques are compressed or removed through catheterization (angioplasty), stripped away from the arterial wall through an incision (endarterectomy) or bypassed with natural or synthetic grafts. These procedures remove the vascular endothelium, disturb the underlying intimal layer, and result in the death of medial SMCs. This injury is followed by medial SMC roliferation and migration into the intima, which typically occurs within the first few weeks nd up to six months after injury and stops when the overlying endothelial cell layer is re-stablished. In humans, these lesions are composed of about 20% cells and 80% extracellular matrix.

In about 30% or more of patients treated by angioplasty, endarterectomy or bypass grafts, thrombosis and/or SMC proliferation in the intima causes re-occlusion of the vessel and consequent failure of the reconstructive surgery. This closure of the vessel subsequent to surgery is known as restenosis.

Modified FVIIa (FVIIai) has been shown to effectively suppress the restenosis process possibly as a result of a decreased procoagulant activity and thrombin generation initially after treatment of the constricted vessel.

For long term prophylactic treatment and increased compliance it would be desirable to have access to low-molecular-weight compounds which may be administered via a route other than intravenously and which have an inhibitory effect on fVIIa-TF activity similar to that of fVIIai. Related patent applications covering low-molecular-weight compounds which down-regulate FVIIa-TF activity include;

JP 07242538 which describes naphthalene derivatives with tissue factor antagonist activity, U.S. Pat. No. 5,639,739 which describes peptide analogues derived from imidazolyl-boronic acid inhibiting FVIIa. Patent applications covering compounds based on peptides from TFPI, JP 6157591 describes compounds based on TFPI-derived peptides with FVIIa-TF antagonist activity, WO 90/03390, WO 95/00541, WO 96/18653, and EP 500 800 describe compounds based on FVIIa-derived peptides with FVIIa-TF antagonist activity, Further related references include U.S. Pat. No. 4,315,766 describes 5-substituted 4H-3,1-Benzoxazinone structures with meta/para substituted aryls in the 2-position. The derivatives have been investigated for activity as herbicides;

WO 96/07648 describes substituted amino groups in the 2-position for treatment of inflammation processes;

U.S. Pat. No. 4,745,116 describes 4H-3,1-benzoxazinone structures having substituted oxygen groups in the 2-position;

WO 91/15487 describes 5-substituted 4H-3,1-benzoxazinone structures having substituted alkyl groups in the 2-position.

Bioorg. Med. Chem.Lett. (6) 679, 1996 mentions examples of structures having the 4H-3,1-benzoxazin skeleton, e.g. C1r inhibitors;

Bioorg. Med. Chem. Lett. (7) 2527, 1997 describes structures having the 4H-3,1-benzoxazin skeleton which are inhibitors of serine proteases of the chymotrypsin family, the serinprotease inhibitors being 2-alpha-aminoalkyl derivatives;

J. Med. Chem. (32) 265 1989 1997 describes structures having the 4H-3,1-benzoxazin skeleton which are plasma lipid lowering agents;

J. Med. Chem. (33) 464 1990 describes structures having the 4H-3,1-benzoxazin skeleton which are inhibitors of human leukocyte elastase.

CA 1,092,118 describe 2-phenylsubstituted quinazolin-4-one derivatives which are antiallergic agents;

BE 862,201 describe 2-phenylsubstituted quinazolin-4-one derivatives which are 15 antiallergic agents;

DE 2,654,215 describe 2-phenylsubstituted quinazolin-4-one derivatives which are antiallergic agents.

Egypt. J. Pharm. Sci., 35(1–6), 1–20, 1994 describes 2-thienyl-benzoxazin-4-one derivatives which have been screened for antiinflammatory activity.

DE 3,000,309 describes 2-haloalkenyl-benzoxazin-4-thione derivatives with herbicidal effect.

J. Heterocycl. Chem. 28(8), 2005–12,1991 describes 2-arylsubstituted benzoxazin-4-one derivatives with calcium antagonistic effect.

JP 55147279 describes 2-pyridylsubstituted quinazolin-4-one derivatives with antidepressant and inflammation inhibting effect.

There is still a need in the art for improved compositions having anticoagulant activity which can be administered orally or otherwise non-intravenously at relatively low doses and not producing the undesirable side effects associated with traditional anticoagulant compositions. The present invention fulfills this need by providing anticoagulants that act specifically on fVIIa-TF at sites of injury, and further provides other related advantages such as its effect on the restenosis process. As compared to most other anticoagulants with an effect on the fVIIa-TF activity, the present invention has the advantage that it is a small synthetic molecule suitable for oral administration and for prophylactic treatment of atherosclerotic patients at risk for thrombosis.

SUMMMARY OF THE INVENTION

It has now been found that the activity of FVIIa in complex with TF can be inhibited by compounds with formula I. By this action the initiation of blood coagulation by FVIIa-TF is prevented, avoiding the formation of undesired thrombi.

The present invention thus provides the use of a compound of the general formula I for the preparation of a pharmaceutical composition for the treatment and/or prevention of coagulation-related diseased states.

The present invention also provides novel compounds with the formula I. The compounds are useful for the treatment of coagulation-related diseased states.

It is an object of the present invention to provide compounds having pharmacological activity as inhibitors of FVIIa-TF activity.

It is an object of the present invention to provide compounds with formula I which are potent modulators of the TF-FVIIa pathway of the coagulation process through an inhibitory action on the TF-FVIIa complex.

It is an object of the present invention to provide the use of compounds with the general formula I for the manufacture of a medicament for treatment of coagulation-related diseases. The coagulation-related diseases include, but are not limited to, diseases such as deep vein thrombosis, pulmonary embolism, stroke, disseminated intravascular coagulation (DIC), vascular restenosis, platelet deposition, myocardial infarction, or the prophylactic treatment of mammals with atherosclerotic vessels at risk for thrombosis.

It is an object of the present invention to provide the use of compounds with the general formula I for the manufacture of a medicament for modulating and normalising an impaired haemostatic balance in a mammal.

It is an object of the present invention to provide the use of compounds with the general formula I for the manufacture of a medicament for use as an inhibitor of blood coagulation in a mammal, or for use as an inhibitor of clotting activity in a mammal, or for use as an inhibitor of deposition of fibrin in a mammal, or for use as an inhibitor of fibrin in a mammal.

It is an object of the present invention to provide methods for:

treatment of coagulation-related diseases;

treatment of mammals suffering from deep vein thrombosis, pulmonary embolism, stroke, disseminated intravascular coagulation (DIC), vascular restenosis, platelet deposition and associated disorders, and myocardial infarction;

prophylactic treatment of mammals with atherosclerotic vessels at risk for thrombosis; modulating and normalising an impaired haemostatic balance in a mammal;

inhibiting blood coagulation in a mammal, or inhibiting clotting activity in a mammal, or inhibiting deposition of fibrin in a mammal, or inhibiting fibrin in a mammal.

The mammal is preferably a human.

Further objects will become apparent from the following description.

DETAILED DESCRIPTION OF THE INVENTION

Definitions

As used herein: The term "$C_{1-8}$-alkyl", "$C_{2-8}$-alkenyl", "$C_{2-8}$-alkynyl" as used herein, alone or in combination, refers to a straight or branched, saturated or unsaturated hydrocarbon chain. The $C_{1-8}$-alkyl residues include aliphatic hydrocarbon residues, unsaturated aliphatic hydrocarbon residues, alicyclic hydrocarbon residues. Examples of the aliphatic hydrocarbon residues include saturated aliphatic hydrocarbon residues having 1 to 8 carbon atoms such as methyl, ethyl, n-propyl, isopropyl, n-butyl, isobutyl, sec.butyl, tert.butyl, n-pentyl, isopentyl, neopentyl, tert.pentyl, n-hexyl, isohexyl. Example of the unsaturated aliphatic hydrocarbon residues include those having 2 to 6 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, ethynyl, 1-propionyl, 2-propionyl, 1-butynyl, 2-butynyl, 3-butynyl, 1-pentynyl, 2-pentynyl, 3-pentenyl, 4-pentenyl, 1-hexynyl, 3-hexynyl, 2,4-hexadiynyl, 5-hexynyl.

The term $C_{3-8}$-cycloalkyl means an alicyclic hydrocarbon residue including saturated alicyclic hydrocarbon residues having 3 to 6 carbon atoms such as cyclopropyl, cyclobutyl, cyclopentyl, cyclohexyl; and $C_{5-6}$ unsaturated alicyclic hydrocarbon residues having 5 to 6 carbon atoms such as 1-cyclopentenyl, 2-cyclopentenyl, 3-cyclopentenyl, 1-cyclohexenyl, 2-cyclohexenyl, 3-cyclohexenyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{1-6}$-alkylthio" as used herein, alone or in combination, refers to a straight or branched monovalent substituent comprising a $C_{1-6}$-alkyl group linked through an thioether sulfur atom having its free valence bond from the thioether sulfur and having 1 to 6 carbon atoms.

The terms "aryl" and "heteroaryl" as used herein refers to an aryl which can be optionally substituted or a heteroaryl which can be optionally substituted and includes phenyl, biphenyl, indene, fluorene, naphthyl (1-naphthyl, 2-naphthyl), anthracene (1-anthracenyl, 2-anthracenyl, 3-anthracenyl), thiophene (2-thienyl, 3-thienyl), furyl (2-furyl, 3-furyl), indolyl, oxadiazolyl, isoxazolyl, quinazolin, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b] furanyl (2-benzo[b]furanyl, 3-benzo[b]furanyl, 4-benzo[b] furanyl, 5-benzo[b]furanyl, 6-benzo[b]furanyl, 7-benzo[b] furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b] furanyl), benzo[b]thiophenyl (2-benzo[b]thiophenyl, 3-benzo[b]thiophenyl, 4-benzo[b]thiophenyl, 5-benzo[b] thiophenyl, 6-benzo[b]thiophenyl, 7-enzo[b]thiophenyl), 2,3-dihydro-benzo[b]thiophenyl (2-(2,3-dihydro-benzo[b] thiophenyl), 3-(2,3-dihydro-benzo[b]thiophenyl), 4-(2,3-dihydro-benzo[b]thiophenyl), 5-(2,3-dihydro-benzo[b] thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indoly, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f] azepine-2-yl, 10,11-dihydro-5H-dibenz[b,f]azepine-3-yl, 10,11-dihydro-5H-dibenz[b,f]azepine-4-yl,10,11-dihydro-5H-dibenz[b,f]azepine-5-yl).

The invention also relates to partly or fully saturated analogues of the ring systems mentioned above.

The term "leaving group" includes, but is not limited to, halogen, sulfonate or an acyl group. Suitable leaving groups will be known to a person skilled in the art.

"Coupling agent" means an agent suitable for formation of acid derivatives from acids or activated acids and amines, phenols, alcohols, or acids including, but not limited to hydroxy-benzotriazole (HOBt) an d de rivatives thereof and carbode imides like dicyclohexylcarbodiimide and ethydimethylamin opropyl carbodibmide (DCC, EDAC). Suitable coupling agents will be known to the skilled person. Activated acids includes acid chlorides, acid anhydrides, esters, and similar derivatives.

"Agent capable of introducing ring closure" means an agent capable of introducing combined hydrolysis and ring closure under absorption of water including, but not limited to, acid anhydrides, both organic like acetic anhydride and inorganic like $P_2O_5$, mineral acids such as concentrated sulfuric acid, phosphoric acid and the like, acid chlorides like $SOCl_2$, $PCl_5$, and $POCl_3$.

"Halogen" refers to fluorine, chlorine, bromine, and iodine. "Halo" refers to fluoro, chloro, bromo and iodo. "Halo-alkyl" means the group —R-halo in which R is alkyl, and both alkyl and halo are as defined herein. The alkyl group may bear one, two or three halo substituents; examples include, but are not limited to, fluoromethyl, difluoromethyl, trifluoromethyl, chloromethyl, dichloromethyl, trichloromethyl, chloroethyl, dichloroethyl, bromoethyl, iodoethyl, and the like.

"Optional" or "optionally" means that the subsequently described event or circumstances may or may not occur, and that the description includes instances where said event or circumstance occur and instances in which is does not. For example, "aryl . . . optionally substituted" means that the aryl may or may not be substituted and that the description includes both unsubstituted aryls and aryls wherein there is substitution.

"Pharmaceutical acceptable acid addition salt" refers to those salts which retain the biological effectiveness and properties of the free bases and which are not biologically or otherwise undesirable, formed with non-toxic acids, either inorganic acids such as hydrochloric acid, sulphuric acid and phosphoric acid, or organic acids such as formic acid, acetic acid, propionic acid, succinic acid, gluconic acid, lactic acid, citric acid, ascorbic acid, benzoic acid, embonic acid, methanesulphonic acid and malonic acid and the like.

"Treatment" means the administration of an effective amount of a therapeutically active compound of the invention with the purpose of preventing any symptoms or disease state to develop or with the purpose of curing or easing such symptoms or disease states already developed. The term "treatment" is thus meant to include prophylactic treatment.

"Coagulation-related disease states": Diseases or symptoms which are caused by unwanted blood coagulation, clotting activity, deposition of fibrin and/or platelets or TF-FVIIa activity. Such diseases include, but are not limited to, deep vein thrombosis, pulmonary embolism, stroke, disseminated intravascular coagulation (DIC), vascular restenosis, platelet deposition, or myocardial infarction, or the prophylactic treatment of mammals with atherosclerotic vessels at risk for thrombosis.

"Inhibitors of FVIIa-TF activity": It has now been found that compounds with the general formulas I or II inhibit FVIIa-TF in in vitro assays of amidolytic and proteolytic activity and thus are able to prolong the TF-induced coagulation in human plasma. They may do so by inhibiting FVIIa activity, by inhibiting FVIIa-TF activity, by preventing the formation of a FVIIa-TF complex or by preventing the activation of factor X by FVIIa-TF. Compounds which solely inhibit the proteolytic activity of FVIIa-TF and/or prolong the coagulation time may do so by preventing the association of factor X with the FVIIa-TF complex or by preventing the activation of factor X bound to the complex.

"Modulators of the TF-FVIIa pathway": Compounds that modulate the coagulation process through an inhibitory action on the TF-FVIIa complex or on TF activity. The activity of FVIIa in complex with TF, in particular its activation of factor X, can be inhibited by a low-molecular weight compound. By this action, the initiation and acceleration of the blood coagulation cascade upon exposure of TF to flowing blood is prevented.

"Pharmaceutically acceptable carriers" means any and all solvents, dispersion media, coatings, antifungal agents, preservatives, isotonic agents and the like.

"Modulating and normalizing an impaired haemostatic balance" means achieving an effect on the coagulation system measurable in in vitro assays and/or animal models which effect diminishes the risk for thrombosis or bleedings.

Certain of the compounds of the invention have chiral centers and exist as optical antipodes. The invention described and claimed herein includes each of the individual enantiomers as well as their racemic modifications and the racemic mixture.

The compounds of this invention use the numbering system set forth below:

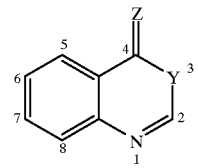

Abreviations

| | |
|---|---|
| TF | Tissue factor |
| FVII or fVII | factor VII |
| FVIIa or fVIIa | activated factor VII |
| FVIIa-TF | complex between activated factor VII and tissue factor initiating blood coagulation |

The present invention relates to the use of compounds of formula I

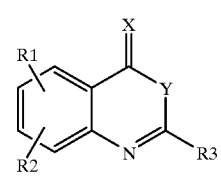

(I)

wherein
  X and Y is independently O, S or NH;
  $R^1$ and $R^2$ independently are
    $C_{1-8}$-alkyl, $C_{2-8}$ alkenyl, $C_{2-8}$ alkynyl, or $C_{3-8}$ cycloalkyl, each optionally substituted with halogen, OH, $NH_2$, $NHR^4$, $N(R^4)_2$, $NHCOR^4$, $C_{1-4}$ alkoxy, trifluoromethoxy, carbamoyl, $CONHR^4$, or $CON(R^4)_2$;

H, Halogen, $CF_3$, $CF_{1-6}$ alkoxy, $C_{1-6}$ alkylthio, $OCF_3$, COOH, ON, $CONH_2$, $CONHR^4$, OH, $NH_2$, $NHR^4$, $N(R^4)_2$, $NHCOR^4$, $CON(R^4)_2$, $CONHSO_2R^4$, $SO_2NH_2$, $SO_2NHR^4$, $C_{1-4}$ alkoxycarbonyl, phenyl, alkylphenyl, or tetrazole;

$R^3$ is aryl or heteroaryl, each optionally substituted with one or more $C_{1-8}$-alkyl, $C_{2-8}$ alkenyl, $C_{2-8}$ alkynyl, or $C_{3-6}$ cycloalkyl, each optionally substituted with halogen, OH, $NH_2$, $NHR^4$, $N(R^4)_2$, $NHCOR^4$, $C_{1-4}$ alkoxy, trifluoromethoxy, carbamoyl, $CONHR^4$, or $CON(R^4)_2$;

Halogen, $CF_3$, $C_{1-6}$ alkoxy, $C_{1-6}$ alkylthio, $OCF_3$, COOH, CN, $CONH_2$, $CONHR^4$, OH, $NH_2$, $HR^4$, $N(R^4)_2$, $NHCOR^4$, $CON(R^4)_2$, $CONHSO_2R^4$, $SO_2NH_2$, $SO_2NHR^4$, phenyl, alkylphenyl, or tetrazole;

$R^4$ is $C_{1-4}$-alkyl, $C_{2-4}$ alkenyl, $C_{2-4}$ alkynyl, $C_{3-6}$ cycloalkyl, or phenyl;

or pharmaceutical acceptable salts thereof, for use as anti-coagulants.

Preferred $R^1$ and $R^2$ are: hydrogen, 4-fluoro, 5-methyl, 6-methyl, 6-fluoro, 5,8-dichloro, 6-chloro, 6-iodo,7-chloro, 5-nitro, 5-amino, 5-acetylamino, 6-nitro, 6-acetylamino, 6-carboxy.

Preferred $R^3$ are: 2,6-difluorophenyl, 2-fluoro, 6-chlorophenyl, 2-fluorophenyl, 2,3-dichlorophenyl, 2-bromophenyl, 2-bromo-5-methoxyphenyl, 2-trifluoromethoxyphenyl, 7-benzofuranyl, 2-thienyl, 2-furanyl, 5-chloro-2-methoxyphenyl, 5-nitrofuranyl 2-piperidyl, 3-chloro-5-trifluoromethyl-2-pyridyl.

Preferred $R^4$ are: Methyl, ethyl, isopropyl, propyl cyclopropyl, cyclopentyl, cyclohexyl, phenyl.

Preferably, $R^3$ is an ortho-substituted aryl or a heteroaryl ring.

In one aspect the present invention relates to the use of compounds with the general formula I, or pharmaceutical acceptable salts thereof, for the manufacture of a medicament for treatment of coagulation-related diseases, or for modulating and normalizing an impaired haemostatic balance in a mammal.

In one embodiment, the invention relates to the use as an inhibitor of blood coagulation in a mammal, or for use as an inhibitor of clotting activity in a mammal, or for use as an inhibitor of deposition of fibrin in a mammal, or for use as an inhibitor of platelet deposition in a mammal. The coagulation-related diseases comprises diseases such as deep vein thrombosis, pulmonary embolism, stroke, disseminated intravascular coagulation (DIC), vascular restenosis, platelet deposition, or myocardial infarction, or for the prophylactic treatment of mammals with atherosclerotic vessels at risk for thrombosis.

In one embodiment, the compounds have the general formula I, wherei n X is O, and Y is O, S or NH.

In another embodiment, the compounds have the general formula I, wherein X is S, and Y is O, S or NH. In another embodiment, the compounds have the general formula I, wherein X is tNH, and Y is O, S or NH. In another embodiment, the compounds have the general formula I, wherein X is O, and Y is O. In another embodiment, the compounds have the general formula I, wherein X is O, and Y is S. In another embodiment, the compounds have the general formula I, wherein X is O, and Y is NH. In another embodiment, the compounds have the general formula I, wherein X is S, and Y is O. In another embodiment, the compounds have the general formula I, wherein X is S, and Y is S. In another embodiment, the comnpounds have the general formula I, wherein X is S, and Y is NH. In another embodiment, the compounds have the general formula I, wherein X is NH, and Y is O. In another embodiment, the compounds have the general formula I, wherein X is NH, and Y is S. In another embodiment, the compounds have the general formula I, wherein X is NH, and Y is NH.

Preferred are 4H-3,1-benzoxazin-4-ones, 4H-3,1-benzoxazin-4-thiones, quinazolin-4-ones, quinazolin-4-thiones, or benzothiazin-4-one derivatives with the formulas shown below ($R^1$, $R^2$ and $R^3$ as defined in claim 1).

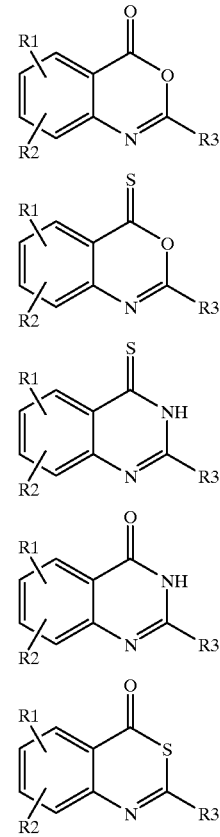

In another aspect the invention relates to the use of compounds with the general formula I for the manufacture of a medicament for modulating and normalizing an impaired haemostatic balance in a mammal.

In another aspect the invention relates to the use of compounds with the general formula I for the manufacture of a medicament for treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis.

The invention also relates to a method for modulating and normalizing an impaired haemostatic balance in a mammal, and to a method for treatment of coagulation-related diseased states in a mammal, which methods comprise administering an effective amount of a compound with formula I, in combination with a pharmaceutical acceptable excipient and/or carrier to the mammal in need of such a treatment.

In one embodiment, the invention relates to a method for treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis, as well as modulating and normalizing an impaired haemostatic balance in a mammal, and a method for inhibiting blood coagulation in a mammal, or inhibiting clotting activity in a mammal, or inhibiting deposition of fibrin in a mammal, or inhibiting fibrin in a mammal, which method comprises administering an effective amount of a compound with formula I, in combination with a pharmaceutically acceptable excipient and/or carrier to the mammal in need of such a treatment.

In another aspect, the invention relates to a method for inhibiting tissue factor activity in a mammal which method comprises administering an effective amount of a compound with formula I, in combination with a pharmaceutical acceptable excipient and/or carrier to the mammal in need of such a treatment.

In one embodiment, the compounds with formula I are selected from the compounds listed in table 1 and table 2, and pharmaceutical acceptable salts thereof.

In another aspect, the invention relates to a method for inhibiting factor VII activity by substantially reducing the ability of activated factor VII to catalyze tissue factor-enhanced activation of factors X and IX comprising administering a compound with formula I, in combination with a pharmaceutical acceptable excipient and/or carrier to a mammal in need of such a treatment.

In another aspect, the invention relates to the use of a compound with formula I for modulating and normalizing an impaired haemostatic balance in a mammal, such as a human, or for the use of a compound with formula I for the treatment of coagulation-related diseased states.

In one embodiment, the coagulation-related diseased states are deep vein thrombosis, pulmonary embolism, stroke, disseminated intravascular coagulation (DIC), vascular restenosis, platelet deposition and associated disorders or myocardial infarction, or the prophylactic treatment of mammals with atherosclerotic vessels at risk for thrombosis.

The invention also relates to novel benzoxazin-4-one derivatives which is selected from a list of 5,8-Dichloro-2-(2-fluoro-phenyl)-4H-3,1-benzoxazin-4-one (1)
6-Methyl-2-thiophen-2-yl-4H-3,1-benzoxazin-4-one (2)
(2,6-Dichloro-phenyl)-6-methyl-4H-3,1-benzoxazin-4-one (3)
6-Methyl-2-(2-trifluoromethoxy-phenyl)-4H-3,1-benzoxazin-4-one (4)
(2,6-Difluoro-phenyl)-6-methyl-4H-3,1-benzoxazin4-one (5)
(2,6-Dimethoxy-phenyl)-6-methyl-4H-3,1-]benzoxazin4-one (6)
(3-Bromo-thiophen-2-yl)-6-methyl-4H-3,1-benzoxazin-4-one (7)
(2,3-Dichloro-phenyl)-6-methyl-4H-3,1-benzoxazin-4-one (8)
2-(2,6-Difluoro-phenyl)-6-methoxy-benzo[d][1,3]oxazin-4-one
2-(2-Fluoro-phenyl)-6-methoxy-benz[d][1,3]oxazin-4-one
2-(2,6-Difluoro-phenyl)-7-trifluoromethyl-benzo[d][1,3]oxazin-4-one
6,7-Difluoro-2-(2-fluoro-phenyl)-benzo[d][1,3]oxazin-4-one
6,7-Difluoro-2-thiophen-2-yl-benzo[d][1,3]oxazin-4-one
6,7-Difluoro-2-furan-2-yl-benzo[d][1,3]oxazin-4-one
2-(2,6-Difluoro-phenyl)-4-oxo-4H-benzo[d][1,3]oxazine-5-carboxylic acid methyl ester
2-(2-Fluoro-phenyl)-4-oxo-4H-benzo[d][1,3]oxazine-5-carboxylic acid methyl ester
4-Oxo-2-thiophen-2-yl-4H-benzo[d][1,3]oxazine-5-carboxylic acid methyl ester
2-Furan-2-yl-4-oxo-4H-benzo[d][1,3]oxazine-5-carboxylic acid methyl ester
2-(2-Methoxy-phenyl)-6-nitro-benzo[d][1,3]oxazin-4-one
2-(2-Methoxy-phenyl)-5-methyl-benzo[d][1,3]oxazin-4-one
2-(2-Methoxy-phenyl)-5-nitro-benzo[d][1,3]oxazin-4-one
6-Nitro-2-(2-nitro-phenyl)-benzo[d][1,3]oxazin-4-one
6-Nitro-2-o-tolyl-benzo[d][1,3]oxazin-4-one
5-Nitro-2-(2-nitro-phenyl)-benzo[d][1,3]oxazin-4-one
5-Nitro-2-(2-nitro-phenyl)-benzo[d][1,3]oxazin-4-one
2-(2-Chloro-pyridin-3-yl)-6-nitro-benzo[d][1,3]oxazin-4-one
2-(2-Chloro-pyridin-3-yl)-5-methyl-benzo[d][1,3]oxazin-4-one
2-(2-Chloro-pyridin-3-yl)-5-nitro-benzo[d][1,3]oxazin-4-one
2-(2,3-Difluoro-phenyl)-6-nitro-benzo[d][1,3]oxazin-4-one
2-(2,3-Difluoro-phenyl)-5-methyl-benzo[d][1,3]oxazin-4-one
2-(2,3-Difluoro-phenyl)-5-nitro-benzo[d][1,3]oxazin-4-one
Acetic acid 2-(6-nitro-4-oxo-4H-benzo[d]1,3)oxazin-2-yl)-phenyl ester
Acetic acid 2-(5-methyl-4-oxo-4H-benzo[d][1,3]oxazin-2-yl)-phenyl ester
Acetic acid 2-(5-nitro-4-oxo-4H-benzo[d][1,3]oxazin-2-yl)-phenyl ester
2-(2,6-Difluoro-phenyl)-6-trifluoromethyl-benzo[d][1,3]oxazin-4-one
2-(2-Fluoro-phenyl)-6-trifluoromethyl-benzo[d][1,3]oxazin-4-one
2-Thiophen-2-yl-6-trifluoromethyl-benzo[d][ 1,3]oxazin-4-one
2-(2,6-Difluoro-phenyl)-5-trifluoromethyl-benzo[d][1,3]oxazin-4-one
2-(2-Fluoro-phenyl)-5-trifluoromethyl-benzo[d][1,3]oxazin-4-one
2-Thiophen-2-yl-5-trifluoromethyl-benzo[d][1,3]oxazin-4-one
2-(2,6-Difluoro-phenyl)-8-trifluoromethyl-benzo[d][1,3]oxazin-4-one
2-(2-Fluoro-phenyl)-8-trifluoromethyl-benzo[d][1,3]oxazin-4-one
2-Furan-2-yl-8-trifluoromethyl-benzo[d][1,3]oxazin-4-one
2-(2-Fluoro-phenyl)-4-oxo-4H-benzo[d][1,3]oxazine-5-carboxylic acid ethyl ester
2-(2,6-Difluoro-phenyl)-7-fluoro-benzo[d][1,3]oxazin-4-one
5-Nitro-2-(5-nitro-furan-2-yl)-benzo[d][1,3]oxazin-4-one
2-(2,3-Dichloro-phenyl)-6,7-difluoro-benzo[d][1,3]oxazin-4-one 6,7-Difluoro-2-(2-trifluoromethoxy-phenyl)-benzo[d][1,3]oxazin-4-one 2-(2,3-Difluoro-phenyl)-6,7-difluoro-benzo[d][1,3]oxazin-4-one 6,7-Difluoro-2-(2-methoxy-phenyl)-benzo[d][1,3]oxazin-4-one 2-(2-Chloro-pyridin-3-yl)-6,7-difluoro-benzo[d][1,3]oxazin-4-one 2-(2,6-Difluoro-phenyl)-6-nitro-benzo[d][1,3]oxazin-4-one (9)

6-Acetamido-(2,6-difluoro-phenyl)-benzo[d][1,3]oxazin-4-one (10)

2-(2,6-Difluoro-phenyl)-5-methyl-benzo[d][1,3]oxazin-4-one (11)

2-(2,6-Difluoro-phenyl)-7-nitro-benzo[d][1,3]oxazin-4-one (12)

2-(2,6-Difluoro-phenyl)-5-nitro-benzo[d][1,3]oxazin-4-one (13)

5-Chloro-2-(2,6-difluoro-phenyl)-benzo[d][1,3]oxazin-4-one (14)

6-Amino-2-(2,6-difluoro-phenyl)-benzo[d][1,3]oxazin-4-one (15)

2-(2,6-Difluoro-phenyl)-8-hydroxy-benzo[d][1,3]oxazin-4-one (16)

5,8-Dichloro-2-(2,6-difluoro-phenyl)-benzo[d][1,3]oxazin-4-one (17)

5-Amino-2-(2,6-difluoro-phenyl)-benzo(d][1,3]oxazin-4-one (18)

2-(2,6-Difluoro-phenyl)-6,7-difluoro-benzo[d][1,3]oxazin-4-one (19)

7-Amino-2-(2,6-difluoro-phenyl)-benzo[d][1,3]oxazin-4-one (20)

and pharmaceutical acceptable salts thereof.

In another aspect, the invention also relates to a pharmaceutical composition comprising a therapeutically active amount of said novel compounds, or a pharmaceutical acceptable salt thereof, in combination with a pharmaceutical acceptable excipient and/or carrier. In one embodiment, the pharmaceutical composition is for oral administration.

Preferred compounds are 2-(2,5-Dimethyl-benzofuran-7-yl)-4H-3,1-benzoxazin-4-one 2-(3-Bromo-phenyl)-4H-3,1-benzoxazin-4-one 2-(3-Bromo-phenyl)-7-chloro-4H-3,1-benzoxazin-4-one 2-(2,4-Dichloro-phenyl)-4H-3,1-benzoxazin-4-one 2-m-Tolyl-4H-3,1-benzoxazin-4-one 2-(2-Fluoro-phenyl)-6-methyl-3,1-benzoxazin-4-one 2-(4-tert-Butyl-phenyl)-7-chloro-4H-3,1-benzoxazin-4-one Naphthalene-2-sulfinic acid [2-(4-oxo-4H-3,1-benzoxazin-2-yl)-phenyl]-amide 2-(4-Chloro-3-nitro-phenyl)-6,7-dimethoxy-4H-3,1-benzoxazin-4-one 2-(5-Chloro-2-methoxy-phenyl)-4H-3,1-benzoxazin-4-one 6-Bromo-2-(5-chloro-2-methoxy-phenyl)-4H-3,1-benzoxazin-4-one 2-(3,4-Dichloro-phenyl)-6,7-dimethoxy-4H-3,1-benzoxazin-4-one 2-(3,4-Dimethyl-phenyl)-4H-3,1-benzoxazin-4-one 7-Chloro-2-(4-methyl-3-nitro-phenyl)-4H-3,1-benzoxazin-4-one 6,7-Dimethoxy-2-p-tolyl-4H-3,1-benzoxazin-4-one 2-phenyl-4H-3,1-benzoxazin-4-one 6,7,8-Trimethoxy-2-(3-trifluoromethyl-phenyl)-4H-3,1-benzoxazin-4-one 6,7-Dimethoxy-2-[2-(4-methoxy-phenoxy)-5-nitro-phenyl]-[4H-3,1-benzoxazin-4-one 5-Chloro-2-[2-(4-methoxy-phenoxy)-5-nitro-phenyl]-4H-3,1-benzoxazin-4-one 2-(4-tert-Butyl-phenyl)-7-chloro-4H-3,1-benzoxazin-4-one 7-Chloro-2-m-tolyl-4H-3,1-benzoxazin-4-one 6,7-Dimethoxy-2-(5-methyl-2-nitro-phenyl)-4H-3,1-benzoxazin-4-one 7-Chloro-2-(4-chloro-3-nitro-phenyl)-4H-3,1-benzoxazin-4-one 2-(3,4-Dimethyl-phenyl)-6,7-dimethoxy-4H-3,1-benzoxazin-4-one 7-Chloro-2-[4-(5-ethyl-pyridin-2-yl)-phenyl]-4H-3,1-benzoxazin-4-one 2-(4-Chloro-3-nitrophenyl)-6,7,8-trimethoxy-4H-3,1-benzoxazin-4-one 2-(2,6-Difluorophenyl)-5-fluoro-4H-3,1-benzoxazin-4-one 2-(2-Fluorophenyl)-4H-3,1-benzoxazin-4-one 5-Chloro-2-(3-trifluoromethylphenyl)-4H-3,1-benzoxazin-4-one 2-(3,4-Dichloro-phenyl)-6-nitro-4H-3,1-benzoxazin-4-one 2-(2-Chloro-6-fluorophenyl)-5-fluoro-3,1-benzoxazin-4-one 7-Chloro-2-(2-fluorophenyl)-3,1-benzoxazin-4-one 2-(2-Chloro-6-fluorophenyl)-6-methyl-4H-3,1-benzoxazin-4-one 2(2-(4-Fluorophenylsulfonyl)amidophenyl)-4H-3,1-benzoxazin-4-one 2-(2-Bromo-5-methoxy-phenyl)-4H-3,1-benzoxazin-4-one 2-(2-Chloromethyl-phenyl)-4H-3,1-benzoxazin-4-one 2-(4-tert-Butyl-phenyl)-6,8-dimethyl-4H-3,1-benzoxazin-4-one 2-(2-Chloro-phenyl)-6-methyl-4H-3,1-benzoxazin-4-one 7-Chloro-2-(3-chloromethyl-phenyl)-4H-3,1-benzoxazin-4-one 2-(2-Chloro-phenyl)-6-iodo-4H-3,1-benzoxazin-4-one 7-Chloro-2-(2-chloro-5-nitro-phenyl)-4H-3,1-benzoxazin-4-one 2-(2-Bromo-phenyl)-6-chloro-4H-3,1-benzoxazin-4-one 6,7-Dimethoxy-2-(3-nitro-phenyl)-4H-3,1-benzoxazin-4-one 2-(3-Nitro-phenyl)4H-3,1-benzoxazin-4-one 7-chloro-2-(2,4-dichlorophenyl)-4H-3,1-benzoxazin-4-on 2-(2,4-Dichloro-phenyl)-6-iodo-4H-3,1-benzoxazin-4-one 6-Bromo-2-(3-chloro-5-trifluoromethyl-pyridin-2-yl)-4H-3,1-benzoxazin-4-one 6-(6,7-Dimethoxy-4-oxo-4H-3,1-benzoxazin-2-yl)-pyridine-2-carboxylic acid methyl ester 6,7-Dimethoxy-2-pyridin-4-yl-4H-3,1-benzoxazin-4-one 6-Bromo-2-pyridin-4-yl-4H-3,1-benzoxazin-4-one 5-Fluoro-2-(2-phenoxy-pyridin-3-yl)-4H-3,1-benzoxazin-4-one 6,7,8-Trimethoxy-2-(2-phenoxy-pyridin-3-yl)-4H-3,1-benzoxazin-4-one 2-(3-Chloro-5-trifluoromethyl-pyridin-2-yl)-6,7-dimethoxy-4H-3,1-benzoxazin-4-one 2-Thiophen-2-yl-4H-3,1-benzoxazin-4-one 6,7,8-Trimethoxy-2-(5-nitro-furan-2-yl)-4H-3,1-benzoxazin-4-one 6-Methyl-2-(5-nitro-furan-2-yl)-4H-3,1-benzoxazin-4-one 2-(2,4-Dichloro-phenyl)-6-nitro-benzo[d][1,3]oxazin-4-one)

6,8-Dibromo-2-(2-fluoro-phenyl)-benzo[d][1,3]oxazin-4-one

7-Chloro-2-(2-chloromethyl-phenyl)-4H-3,1-benzoxazin-4-one (table 1)
and 5,8-Dichloro-2-(2-fluoro-phenyl)-4H-3,1-benzoxazin-4-one 6-Methyl-2-thiophen-2-yl-4H-3,1-benzoxazin-4-one 2-(2,6-Dichloro-phenyl)-6-methyl-4H-3,1-benzoxazin-4-one 6-Methyl-2-(2-trifluoromethoxy-phenyl)-4H-3,1-benzoxazin-4-one 2-(2,6-Difluoro-phenyl)-6-methyl-4H-3,1-benzoxazin-4-one 2-(2,6-Dimethoxy-phenyl)-6-methyl-4H-3,1-]benzoxazin-4-one 2-(3-Bromo-thiophen-2-yl)-6-methyl-4H-3,1-benzoxazin-4-one 2-(2,3-Dichloro-phenyl)-6-methyl-4H-3,1-benzoxazin-4-one 2-(2,6-Difluoro-phenyl)-6-methoxy-benzo[d][1,3]oxazin-4-one 2-(2-Fluoro-phenyl)-6-methoxy-benzo[d][1,3]oxazin-4-one 2-(2,6-Difluoro-phenyl)-7-trifluoromethyl-benzo[d][1,3]oxazin-4-one 6,7-Difluoro-2-(2-fluoro-phenyl)-benzo[d][1,3]oxazin-4-one 6,7-Difluoro-2-thiophen-2-yl-benzo[d][1,3]oxazin-4-one 6,7-Difluoro-2-furan-2-yl-benzo[d][1,3]oxazin-4-one 2-(2,6-Difluoro-phenyl)-4-oxo-4H-benzo[d][1,3]oxazine-5-carboxylic acid methyl ester 2-(2-Fluoro-phenyl)-4-oxo-4H-benzo[d][1,3]oxazine-5-carboxylic acid methyl ester 4-Oxo-2-thiophen-2-yl-4H-benzo[d][1,3]oxazine-5-carboxylic acid methyl ester 2-Furan-2-yl-4-oxo-4H-benzo[d][1,3]oxazine-5-carboxylic acid methyl ester 2-(2-Methoxy-phenyl)-6-nitro-benzo[d][1,3]oxazin-4-one 2-(2-Methoxy-phenyl)-5-methyl-benzo[d][1,3]oxazin-4-one 2-(2-Methoxy-phenyl)-5-nitro-benzo[d][1,3]oxazin-4-one 6-Nitro-2-(2-nitro-phenyl)-benzo[d][1,3]oxazin-4-one 6-Nitro-2-o-tolyl-benzo[d][1,3]oxazin-4-one 5-Nitro-2-(2-nitro-phenyl)-benzo[d][1,3]oxazin-4-one 5-Nitro-2-(2-nitro-phenyl)-benzo[d][1,3]oxazin-4-one 2-(2-Chloro-pyridin-3-yl)-6-nitro-benzo[d][1,3]oxazin-4-one 2-(2-Chloro-pyridin-3-yl)-5-methyl-benzo[d][1,3]oxazin-4-one 2-(2-Chloro-pyridin-3-yl)-5-nitro-benzo[d][1,3]oxazin-4-one 2-(2,3-Difluoro-phenyl)-6-nitro-benzo[d][1,3]oxazin-4-one 2-(2,3-Difluoro-phenyl)-5-methyl-benzo[d][1,3]oxazin-4-one 2-(2,3-Difluoro-phenyl)-5-nitro-benzo[d][1,3]oxazin-4-one Acetic acid 2-(6-nitro-4-oxo-4H-benzo[d][1,3]oxazin-2-yl)-phenyl ester Acetic acid 2-(5-methyl-4-oxo-4H-benzo[d][1,3]oxazin-2-yl)-phenyl ester Acetic acid 2-(5-nitro4-oxo-4H-benzo[d][1,3]oxazin-2-yl)-phenyl ester 2-(2,6-Difluoro-phenyl)-6-trifluoromethyl-benzo[d][1,3]oxazin-4-one 2-(2-Fluoro-phenyl)-6-trifluoromethyl-benzo[d][1,3]oxazin-4-one 2-Thiophen-2-yl-6-trifluoromethyl-benzo[d][1,3)oxazin-4-one 2-(2,6-Difluoro-phenyl)-5-trifluoromethyl-benzo[d][1,3]oxazin-4-one 2-(2-Fluoro-phenyl)-5-trifluoromethyl-benzo[d][1,3]oxazin-4-one 2-Thiophen-2-yl-5-trifluoromethyl-benzo[d][1,3]oxazin-4-one 2-(2,6-Difluoro-phenyl)-8-trifluoromethyl-benzo[d][1,3]oxazin-4-one 2-(2-Fluoro-phenyl)-8-trifluoromethyl-benzo[d][1,3]oxazin-4-one 2-Furan-2-yl-8-trifluoromethyl-benzo[d][1,3]oxazin-4-one 2-(2-Fluoro-phenyl)-4-oxo-4H-benzo[d][1,3]oxazine-5-carboxylic acid ethyl ester 2-(2,6-Difluoro-phenyl)-7-fluoro-benzo[d][1,3]oxazin-4-one 5-Nitro-2-(5-nitro-furan-2-yl)-benzo[d][1,3]oxazin-4-one 2-(2,3-Dichloro-phenyl)-6,7-difluoro-benzo[d][1,3]oxazin-4-one 6,7-Difluoro-2-(2-trifluoromethoxy-phenyl)-benzo[d][1,3]oxazin-4-one 2-(2,3-Difluoro-phenyl)-6,7-difluoro-benzo[d][1,3]oxazin-4-one 6,7-Difluoro-2-(2-methoxy-phenyl)-benzo[d][1,3]oxazin-4-one 2-(2-Chloro-pyridin-3-yl)-6,7-difluoro-benzo[d][1,3]oxazin-4-one 2-(2,6-Difluoro-phenyl)-6-nitro-benzo[d][1,3]oxazin-4-one 6-Acetamido-(2,6-difluoro-phenyl)-benzo[d][1,3]oxazin-4-one 2-(2,6-Difluoro-phenyl)-5-methyl-benzo[d][1,3]oxazin-4-one 2-(2,6-Difluor-phenyl)-7-nitro-benzo[d][1,3]oxazin-4-one 2-(2,6-Difluoro-phenyl)-5-nitro-benzo[d][1,3]oxazin-4-one 5-Chloro-2-(2,6-difluoro-phenyl)-benzo[d][1,3]oxazin-4-one 6-Amino-2-(2,6-difluoro-phenyl)-benzo[d][1,3]oxazin-4-one 2-(2,6-Difluoro-phenyl)-8-hydroxy-benzo[d][1,3]oxazin-4-one 5,8-Dichloro-2-(2,6-difluoro-phenyl)-benzo[d][1,3]oxazin-4-one 5-Amino-2-(2,6-difluoro-phenyl)-benzo[d][1,3]oxazin-4-one 2-(2,6-Difluoro-phenyl)-6,7-difluoro-benzo[d][1,3]oxazin-4-one 7-Amino-2-(2,6-difluoro-phenyl)-benzo[d][1,3]oxazin-4-one (table 2)
and pharmaceutical acceptable salts thereof.

Preparation of Compounds with Formula I

The compounds with general formula I may be prepared by methods which comprise:

A) reacting a compound of formula II

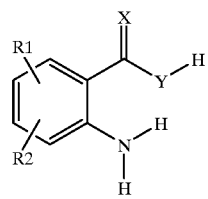

(II)

with a compound of the formula $R^3COL$; $R^1, R^2, R^3$, X, and Y having the meanings described above, L being a good leaving group such as halogen, sulfate, or acyl group.

or

B)
  1) reacting a compound of formula II

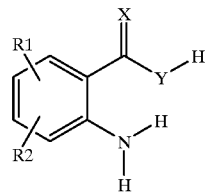

(II)

with a compound of the formula $R^3COOH$, under formation of a structure III

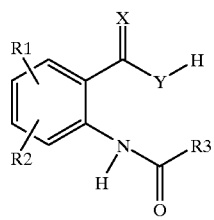

(III)

$R^1, R^2, R^3$, X, and Y having the meanings described above, using standard coupling reagents as HOBt and carbodiimides like DCC, EDAC or similar agents known to be suitable for formation of amide bonds from acids or activated acids and amines.

and, subsequently, 2) reacting a compound of the formula III

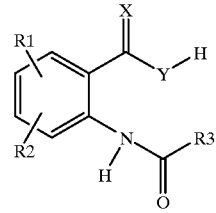

(III)

with an agent capable of introducing ring closure to form a structure of the formula I.

Such agents can be carboxylic acid anhydrides such as acetic anhydride, concentrated sulfuric acid, $POCl_3$. $P_2O_5$ or similar agents.

This ring closure might be performed directly after an amide formation as described above or from amides of the formula III prepared by other routes or purchased.

or

C) reacting a compound of the formula III

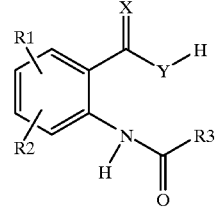

(III)

with an agent capable of introducing ring closure to form a structure of the formula I.

Such agents can be carboxylic acid anhydrides such as acetic anhydride, concentrated sulfuric acid, $POCl_3$. $P_2O_5$ or similar agents.

This ring closure might be performed directly after an amide formation as described above or from amides of the formula III prepared by other routes or purchased.

or

D) reaction of a structure of the formula IV

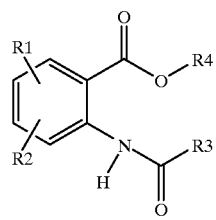

(IV)

in which $R^1$, $R^2$, and $R^3$ has the meaning described above and $R^4$ is an $C_{1-8}$ alkyl group with an agent capable of introducing ring closure like conc. $H_2SO_4$ or similar agents which can introduce combined hydrolysis and ring closure under absorption of water.

The different methods may be schematically illustrated as follows:

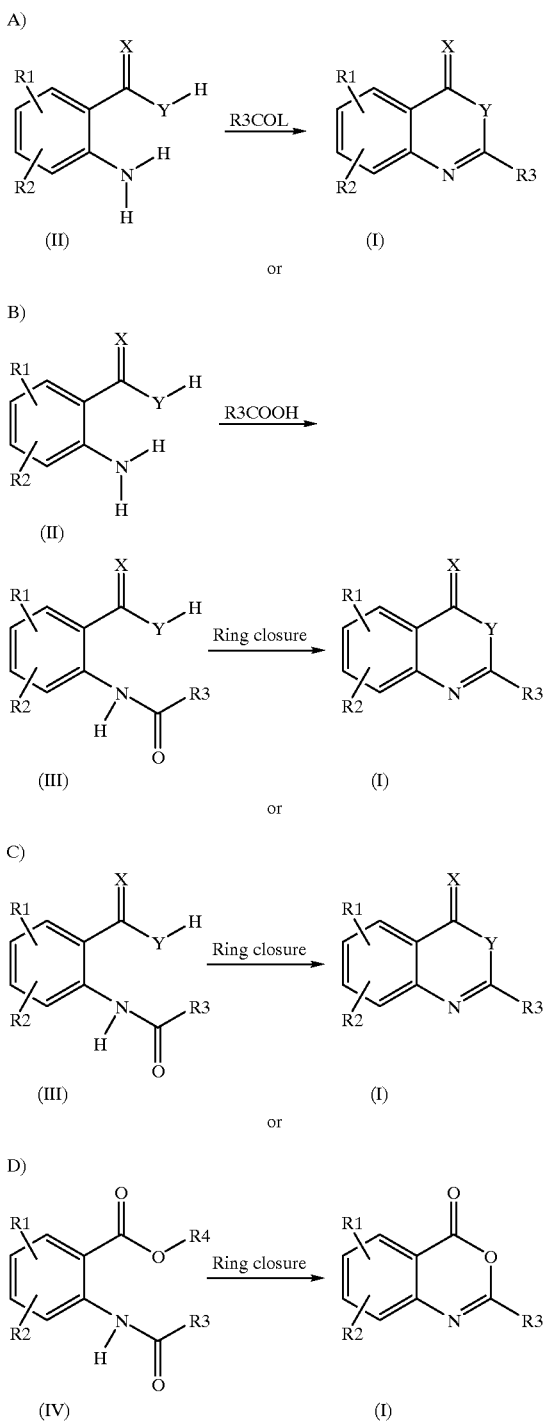

Examples of the synthetic methods described above are known to a person skilled in the art and described several places in the literature; see for example, E. P. Papadopoulos and C. D. Torres: Heterocycles 19 (6) 1039–1042, 1982;
J. L. Gilmore et al:. Bioorganic and Medicinal Chemistry Letters 6 (6), 679–682, 1996;
M Davies, R. J. Hook, Wen Yang Wu: J. Heterocyclic. Chem. 21 369–373, 1984;
G. Hamprecht, B. Wuerzer: U.S. Pat. No. 4,315,766, 1982;

and in references found therein.

Some of the structures described in the present invention are commercially available from companies selling special chemicals. Examples are companies like Maybridge and Salor.

Examples of compounds of formula I are the following:

2-(2,5-Dimethyl-benzofuran-7-yl)-4H-3,1-benzoxazin-4-one
2-(3-Bromo-phenyl)-4H-3,1-benzoxazin-4-one
2-(3-Bromo-phenyl)-7-chloro-4H-3,1-benzoxazin-4-one
2-(2,4-Dichloro-phenyl)-4H-3,1-benzoxazin-4-one
2-m-Tolyl-4H-3,1-benzoxazin-4-one
2-(2-Fluoro-phenyl)-6-methyl-3,1-benzoxazin-4-one
2-(4-tert-Butyl-phenyl)-7-chloro-4H-3,1-benzoxazin-4-one
Naphthalene-2-sulfinic acid [2-(4-oxo-4H-3,1-benzoxazin-2-yl)-phenyl]-amide
2-(4-Chloro-3-nitro-phenyl)-6,7-dimethoxy-4H-3,1-benzoxazin-4-one
2-(5-Chloro-2-methoxy-phenyl)-4H-3,1-benzoxazin-4-one
6-Bromo-2-(5-chloro-2-methoxy-phenyl)-4H-3,1-benzoxazin-4-one
2-(3,4-Dichloro-phenyl)-6,7-dimethoxy-4H-3,1-benzoxazin-4-one
2-(3,4-Dimethyl-phenyl)-4H-3,1-benzoxazin-4-one
7-Chloro-2-(4-methyl-3-nitro-phenyl)-4H-3,1-benzoxazin-4-one
6,7-Dimethoxy-2-p-tolyl-4H-3,1-benzoxazin-4-one
2-phenyl-4H-3,1-benzoxazin-4-one
6,7,8-Trimethoxy-2-(3-trifluoromethyl-phenyl)-4H-3,1-benzoxazin-4-one
6,7-Dimethoxy-2-[2-(4-methoxy-phenoxy)-5-nitro-phenyl]-4H-3,1-benzoxazin-4-one
5-Chloro-2-[2-(4-methoxy-phenoxy)-5-nitro-phenyl]-4H-3,1-benzoxazin-4-one
2-(4-tert-Butyl-phenyl)-7-chloro-4H-3,1-benzoxazin-4-one
7-Chloro-2-m-tolyl-4H-3,1-benzoxazin-4-one
6,7-Dimethoxy-2-(5-methyl-2-nitro-phenyl)-4H-3,1-benzoxazin-4-one
7-Chloro-2-(4-chloro-3-nitro-phenyl)-4H-3,1-benzoxazin-4-one
2-(3,4-Dimethyl-phenyl)-6,7-dimethoxy-4H-3,1-benzoxazin-4-one
7-Chloro-2-[4-(5-ethyl-pyridin-2-yl)-phenyl]-4H-3,1-benzoxazin-4-one
2-(4-Chloro-3-nitrophenyl)-6,7,8-trimethoxy-4H-3,1-benzoxazin-4-one
2-(2,6-Difluorophenyl)-5-fluoro-4H-3,1-benzoxazin-4-one
2-(2-Fluorophenyl)-4H-3,1-benzoxazin-4-one
5-Chloro-2-(3-trifluoromethylphenyl)-4H-3,1-benzoxazin-4-one
2-(3,4-Dichloro-phenyl)-6-nitro-4H-3,1-benzoxazin-4-one
2-(2-Chloro-6-fluorophenyl)-5-fluoro-3,1-benzoxazin-4-one
7-Chloro-2-(2-fluorophenyl)-3,1-benzoxazin-4-one
2-(2-Chloro-6-fluorophenyl)-6-methyl-4H-3,1-benzoxazin-4-one 2-(2-(4-Fluorophenylsulfonyl)amidophenyl)-4H-3,1-benzoxazin-4-one
2-(2-Bromo-5-methoxy-phenyl)-4H-3,1-benzoxazin-4-one
2-(2-Chloromethyl-phenyl)-4H-3,1-benzoxazin-4-one
2-(4-tert-Butyl-phenyl)-6,8-dimethyl-4H-3,1-benzoxazin-4-one
2-(2-Chloro-phenyl)-6-methyl-4H-3,1-benzoxazin-4-one
7-Chloro-2-(3-chloromethyl-phenyl)-4H-3,1-benzoxazin-4-one
2-(2-Chloro-phenyl)-6-iodo-4H-3,1-benzoxazin-4-one
7-Chloro-2-(2-chloro-5-nitro-phenyl)-4H-3,1-benzoxazin-4-one
2-(2-Bromo-phenyl)-6-chloro-4H-3,1-benzoxazin-4-one
6,7-Dimethoxy-2-(3-nitro-phenyl)-4H-3,1-benzoxazin-4-one
2-(3-Nitro-phenyl)-4H-3,1-benzoxazin-4-one
7-chloro-2-(2,4-dichlorophenyl)-4H-3,1-benzoxazin-4-one
2-(2,4-Dichloro-phenyl)-6-iodo-4H-3,1-benzoxazin-4-one
6-Bromo-2-(3-chloro-5-trifluoromethyl-pyridin-2-yl)-4H-3,1-benzoxazin-4-one
6-(6,7-Dimethoxy-4-oxo-4H-3,1-benzoxazin-2-yl)-pyridine-2-carboxylic acid methyl ester
6,7-Dimethoxy-2-pyridin-4-yl-4H-3,1-benzoxazin-4-one
6-Bromo-2-pyridin-4-yl-4H-3,1-benzoxazin-4-one
5-Fluoro-2-(2-phenoxy-pyridin-3-yl)-4H-3,1-benzoxazin-4-one
6,7,8-Trimethoxy-2-(2-phenoxy-pyridin-3-yl)-4H-3,1-benzoxazin-4-one
2-(3-Chloro-5-trifluoromethyl-pyridin-2-yl)-6,7-dimethoxy-4H-3,1-benzoxazin-4-one
2-Thiophen-2-yl-4H-3,1-benzoxazin-4-one
6,7,8-Trimethoxy-2-(5-nitro-furan-2-yl)-4H-3,1-benzoxazin-4-one
6-Methyl-2-(5-nitro-furan-2-yl)-4H-3,1-benzoxazin-4-one
5,8-Dichloro-2-(2-fluoro-phenyl)-4H-3,1-benzoxazin-4-one
6-Methyl-2-thiophen-2-yl-4H-3,1-benzoxazin-4-one
2-(2,6-Dichloro-phenyl)-6-methyl-4H-3,1-benzoxazin-4-one
6-Methyl-2-(2-trifluoromethoxy-phenyl)-4H-3,1-benzoxazin-4-one
2-(2,6-Difluoro-phenyl)-6-methyl-4H-3,1-benzoxazin-4-one
2-(2,6-Dimethoxy-phenyl)-6-methyl-4H-3,1-]benzoxazin-4-one
2-(3-Bromo-thiophen-2-yl)-6-methyl-4H-3,1-benzoxazin-4-one
2-(2,3-Dichloro-phenyl)-6-methyl-4H-3,1-benzoxazin-4-one
2-(2,4-Dichloro-phenyl)-6-nitro-benzo[d][1,3]oxazin-4-one
6,8-Dibromo-2-(2-fluoro-phenyl)-benzo[d][1,3]oxazin-4-one
7-Chloro-2-(2-chloromethyl-phenyl)-4H-3,1-benzoxazin-4-one Pharmaceutical Compositions The compounds above may be formulated into pharmaceutical compositions comprising the compounds and a pharmaceutically acceptable carrier or diluent. Such carriers include water, physiological saline, ethanol, polyols, e.g., glycerol or propylene glycol, or vegetable oils. As used herein, "pharmaceutically acceptable carriers" also encompasses any and all solvents, dispersion media, coatings, antifungal agents, preservatives, isotonic agents and the like. Except insofar as any conventional medium is incompatible with the active ingredient and its intended use, its use in the compositions of the present invention is contemplated.

The compositions containing the compounds of this invention may be prepared by conventional techniques and appear in conventional forms, for example, capsules, tablets, solutions or suspensions. The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil and water. Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage. Generally, the dosage range of the compound for a small mammal, such as a rabbit, is 15–50 mmoles per kg of body weight; for larger mammals, such as humans, 5–50 mmoles, preferably about 10–20 mmoles, per kg of body weight, is useful. This corresponds to about 2–25 mg/kg body weight. However, a preferred dosage range is from 1 to about 100 mg/day, or from about 1 to about 100 mg per dose when administered to patients, e.g. humans, as a drug.

A typical tablet which may be prepared by conventional tabletting techniques contains

| | |
|---|---|
| Core: | |
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |
| Coating: | |
| HPMC | approx. 9 mg |
| *Mywacett ® 9-40 T | approx. 0.9 mg |

*Acylated monoglyceride used as plasticizer for film coating.

The route of administration may be any route which effectively transports the active compound to the appropriate or desired site of action, such as oral or parenteral, e.g., rectal, transdermal, subcutaneous, intranasal, intramuscular, topical, intravenous, intraurethral, ophthalmic solution or an ointment, the oral route being preferred.

Due to their high degree of activity, the compounds of the invention may be administered to a subject, e.g. a living animal body, in need of such treatment, elimination, alleviation, or amelioration of an indication such as prolonged bleeding or disorders related to the haemostatic balance, often preferably in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount. Suitable dosage ranges varies as indicated above depending as usual upon the exact mode of administration, form in which administered, the indication towards which the administration is directed, the subject involved and the body weight of the subject involved, and the preference and experience of the physician or veterinarian in charge.

Methods for Identifylng Inhibitory Compounds

The general strategy for identifylng compounds is depicted below:

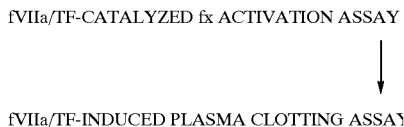

fVIIa/TF-CATALYZED fx ACTIVATION ASSAY fVIIa/TF-INDUCED PLASMA CLOTTING ASSAY

Inhibitory Compounds are Identified in a fX Activation Assay:

The compounds are dissolved in DMSO and mixed with a solution of fVIIa in $Ca^{2+}$-containing buffer (1+5). 30 μl of this mixture was then mixed with 45 μl TF (relipidated in PC/PS vesicles) and 25 μl of a solution containing fX, all in $Ca^{2+}$-containing buffer. This gives final concentrations of 100 pM fVIIa, 5 pM TF, 175 nM fX and various concentrations of the compounds. After a 5-min incubation, the fVIIa/TF-catalyzed activation of fX is terminated by the addition of 50 μl buffer containing enough EDTA to give an excess over the $Ca^{2+}$ ions present. 50 μl of a 2-mM solution of S-2765 (fXa substrate) is then added and the fXa formed is allowed to hydrolyze the substrate for 10 minutes during which the absorbance at 405 nm is continuously monitored in a SPECTRAmax™ 340 plate reader. The slope of the absorption curve is compared to that of a control where DMSO alone was added to fVIIa/TF/fX.

Test of Anticoagulant Potency in a fVIIaTF-initiated Clotting Assay:

The test compounds, 20 mM in DMSO, are diluted in citrated normal human plasma just before the analysis (1+19) and placed in the sample carousel. 55 μl sample (compound in plasma) is mixed with 55 μl of thromboplastin (Innovin, Dade) and incubated for 5 min. The clotting reaction is started by adding 55 μl of a 25-mM $CaCl_2$ solution, ylelding a final compound concentration of 0,33 mM. The clotting time is measured using an ACL 300 R coagulometer. The ratio between the clotting time in the presence and absence of test compound is used to quantify the anticoagulant efficiency.

The compounds with general formula I have interesting pharmacological properties. For example, the compounds of this invention can be used to modulate and normalize an impaired haemostatic balance in mammals caused by deficiency or malfunction of blood clotting factors or their inhibitors. The fVIIa and in particular the fVIIa/TF activity plays an important role in the control of the coagulation cascade, and modulators of this key regulatory activity such as the present invention can be used in the treatment of coagulation-related diseased states.

Preferably the pharmaceutical composition is administered by the oral route. However, the route of administration of the compositions containing a compound of formula I may be any route which effectively transports the active compound to its site of action, such as transdermal, pulmonal, subcutaneous, rectal, etc.

The pharmaceutical composition comprising compounds with formula I may be useful for modulating and normalizing an impaired haemostatic balance in a mammal. In particular, the pharmaceutical composition may be useful for the treatment of coagulation-related diseased states. More particularly the pharmaceutical composition may be useful as an inhibitor of blood coagulation in a mammal, as an inhibitor of clotting activity in a mammal, as an inhibitor of deposition of fibrin in a mammal, as an inhibitor of platelet deposition in a mammal, in the treatment of mammals suffering from deep vein thrombosis, pulmonary embolism, stroke, disseminated intravascular coagulation (DIC), vascular restenosis, platelet deposition and associated disorders, myocardial infarction, and in the prophylactic treatment of mammals with atherosclerotic vessels at risk for developing thrombosis. Throughout this specification the term mammal is also intended to comprise a human.

The regimen for any patient to be treated with the compositions according to the present invention should be determined by those skilled in the art. The daily dose to be administered in therapy can be determined by a physician and will depend on the particular compound employed, on the route of administration and on the age and the condition of the patient. The daily dose comprises an effective amount (i.e. a therapeutically effective amount) of a compound according to the invention wherein the amount can be determined by a physician and will depend on the particular compound employed, on the route of administration and on the age and the condition of the patient. A convenient daily dosage can be in the range of from about 0.1 μmol to about 0.2 mmol of the active ingredient.

Furthermore, the invention relates to a method for inhibiting TF activity in a mammal which method comprises administering an effective amount of a compound of formula I, in combination with a pharmaceutical acceptable excipient and/or carrier to the mammal in need of such a treatment.

The invention also relates to a method for inhibiting fVIIa activity by substantially reducing the ability of activated fVIIa to catalyze TF-enhanced activation of factors X and IX comprising administering a compound with formula I, in combination with a pharmaceutical acceptable excipient and/or carrier to a mammal in need of such a treatment.

The invention also relates to a method for substantially inhibiting the binding of fVII/fVIIa to TF which method comprises administering an effective amount of a compound of formula I, in combination with a pharmaceutical acceptable excipient and/or carrier to the mammal in need of such a treatment.

The compositions with formula I are particularly useful in methods for treating patients when formulated into pharmaceutical compositions, where they may be given by oral administration to individuals suffering from a variety of diseased states to treat coagulation-related conditions.

Among the medical indications for the subject compositions are those commonly treated with anticoagulants, such as, for example, deep vein thrombosis, pulmonary embolism, stroke, disseminated intravascular coagulation (DIC) and myocardial infarction. With an oral administration, the compositions of the invention is particular useful in prophylactic treatment of patients with atherosclerotic vessels at risk for thrombosis. The compositions can also be used to inhibit vascular restenosis and platelet deposition and associated disorders.

Typically for oral administration to humans the pharmaceutical compositions will comprise one or more compounds of the invention and pharmaceutically acceptable carriers and buffers.

Examples of pharmaceutically acceptable salts are pharmaceutically acceptable acid addition salts with non-oxic acids, either inorganic acids such as hydrochloric acid, sulphuric acid and phosphoric acid, or organic acids such as formic acid, acetic acid, propionic acid, succinic acid, gluconic acid, lactic acid, citric acid, ascorbic acid, benzoic acid, embonic acid, methanesulphonic acid and malonic acid.

Pharmaceutical compositions which comprise at least one compound of formula I or a pharmaceutically acceptable acid addition salt thereof in connection with a pharmaceutically acceptable carrier may be in the form of powders, solutions, or suspensions, which may or may not be divided in unit dosage form or in the form of capsules or tablets. A preferred composition is in the form of an composition for oral administering.

The pharmaceutical compositions comprising a compound with formula I or a pharmaceutical acceptable salt thereof may further comprise carriers, diluents, absorption enhancers, tablet disintegrating agents and other ingredients which are conventionally used in the art. The powders and tablets preferably contain from 5 to 99%, more preferred from 10 to 90 of the active ingredient. Examples of solid carriers are magnesium carbonate, magnesium stearate, dextrin, lactose, sugar, talc, gelatin, pectin, tragacanth, methyl cellulose, sodium carboxymethyl cellulose, low melting waxes and cocoa butter. Liquid compositions include sterile solutions, suspensions and emulsions suitable for parenteral injection.

The compositions of this invention are prepared by methods known per se by the skilled art worker (see, for example, Remington: The Science and Practice of Pharmacy, 1995).

The present invention is further illusrated by the following examples which, however, are not to be construed as limiting the scope of protection. The features disclosed in the foregoing description and in the following examples may, both separately and in any combination thereof, be material for realizing the invention in diverse forms thereof.

EXAMPLES

The following examples 1–8 describe synthesis of new compounds according to the invention.

Example 1
5,8-Dichloro-2-(2-fluoro-phenyl)-4H-3,1-benzoxazin-4-one (1).

2-Amino-3,6-dichlorobenzoic acid (0.5 g) and triethyl amine (20 ml) were mixed. 2-Fluorobenzoyl chloride (0.77 g) was added dropwise under cooling and stirring. The mixture was subsequently heated to RT and stirred until disappearance of starting material was seen on TLC (silicagel) using heptane/ethyl acetate (4/1) as eluent. After cooling on ice the precipitate was filtered off and the filtrate evaporated to dryness. The residue was partitioned between methylene chloride and potassium carbonate (2N), the organic layers separated, dried over magnesium sulfate and evaporated to dryness. The raw product was purified by column chromatography on silicagel using heptane/ethyl acetate as eluent. Yield 0.31 g. m.p. 140° C.

Example 2
6-Methyl-2-thiophen-2-yl-4H-3,1-benzoxazin-4-one (2).

2-Amino-5-methylbenzoic acid (0.5 g) and triethyl amine (10 ml) were mixed in dry toluene (20 ml). 2-Thienylcarbonyl chloride (1.07 g) was added dropwise under cooling and stirring. The mixture was subsequently heated to RT for 24 h, then heated to 80° C. for 1 h. After cooling on ice the precipitate was filtered off and the filtrate evaporated to dryness. The residue was partitioned between methylene chloride and potassium carbonate (2N), the organic layers separated, dried over magnesium sulfate and evaporated to dryness. The raw product was purified by column chromatography on silicagel using heptane/ethyl acetate as eluent.

Yield 0.77 g. m.p. 180° C.,

Example 3
2-(2,6-Dichloro-phenyl)-6-methyl-4H-3,1-benzoxazin-4-one (3).

2-Amino-5-methylbenzoic acid (0.5 g) and triethyl amine (10 ml) were mixed in dry toluene (20 ml). 2,6-Dichlorobenzoyl chloride (1.52 g) was added dropwise under cooling and stirring. The mixture was subsequently heated to RT for 24 h, then heated to 80° C. for 1 h. After cooling on ice the precipitate was filtered off and the filtrate evaporated to dryness. The residue was partitioned between methylene chloride and potassium carbonate (2N), the organic layers separated, dried over magnesium sulfate and evaporated to dryness. The raw product was purified by column chromatography on silicagel using heptane/ethyl acetate as eluent.

Yield 0.12g, m.p. 153° C.

Example 4
6-Methyl-2-(2-trifluoromethoxy-phenyl)-4H-3,1-benzoxazin-4-one (4).

2-Amino-5-methylbenzoic acid (0.5 g) and triethyl amine (10 ml) were mixed in dry toluene (20 ml). 2-Trifluoromethoxybenzoyl chloride (1.64 g) was added dropwise under cooling and stirring. The mixture was subsequently heated to RT for 2 days.

After cooling on ice the precipitate was filtered off and the filtrate evaporated to dryness. The residue was partitioned between methylene chloride and potassium carbonate (2N), the organic layers separated, dried over magnesium sulfate and evaporated to dryness. The raw product was purified by column chromatography on silicagel using heptane/ethyl acetate as eluent. Yield 1.06 g. m.p. 70–80° C.

Example 5
2-(2,6-Difluoro-phenyl)-6-methyl-4H-3,1-benzoxazin-4-one (5).

2-Amino-5-methylbenzoic acid (0.5 g) and triethyl amine (10 ml) were mixed in dry toluene (20 ml). 2,6-Difluorobenzoyl chloride (1.28 g) was added dropwise under cooling and stirring. The mixture was subsequently heated to RT for 2 days. After cooling on ice the precipitate was filtered off and the filtrate evaporated to dryness.

The residue was partitioned between methylene chloride and potassium carbonate (2N), the organic layers separated, dried over magnesium sulfate and evaporated to dryness. The raw product was purified by column chromatography on silicagel using heptane/ethyl acetate as eluent. Yield 0.9 g. m.p. 156° C.

Example 6
2-(2,6-Dimethoxy-phenyl)-6-methyl-4H-3,1-lbenzoxazin-4-one (6).

2-Amino-5-methylbenzoic acid (0.5 g) and triethyl amine (10 ml) were mixed in dry toluene (20 ml). 2,6-Dimethoxyobenzoyl chloride (1.46 g) was added dropwise under cooling and stirring. The mixture was subsequently heated to RT for 2 days. After cooling on ice the precipitate was filtered off and the filtrate evaporated to dryness. The residue was partitioned between methylene chloride and potassium carbonate (2N), the organic layers separated, dried over magnesium sulfate and evaporated to dryness. The raw product was purified by column chromatography on silicagel using heptane/ethyl acetate as eluent. Yield 0.98 g. m.p. 161° C.

Example 7
2-(3-Bromo-thiophen-2-yl)-6-methyl-4H-3,1-benzoxazin-4-one (7),

2-Amino-5-methylbenzoic acid (0.5 g) and triethyl amine (10 ml) were mixed in dry toluene (20 ml). 3-Bromo-2-thienylcarbonyl chloride (0.72 g) was added dropwise under cooling and stirring. The mixture was subsequently heated to RT for 2 days.

After cooling on ice the precipitate was filtered off and the filtrate evaporated to dryness. The residue was partitioned between methylene chloride and potassium carbonate (2N), the organic layers separated, dried over magnesium sulfate and evaporated to dryness. The raw product was purified by column chromatography on silicagel using heptane/ethyl acetate as eluent. Yield 0.09 g. m.p. 159° C.

Example 8
2-(2,3-Dichloro-phenyl)-6-methyl-4H-3,1-benzoxazin-4-one (8).

2-Amino-5-methylbenzoic acid (0.5 g) and dry pyridine (20 ml) were mixed in dry toluene (20 ml). 3-Bromo-2-thienylcarbonyl chloride (0.72 g) was added dropwise under cooling and stirring. The mixture was subsequently heated to 80° C. for 1 h.

After cooling on ice the precipitate was filtered off and the filtrate evaporated to dryness. The residue was partitioned between methylene chloride and potassium carbonate (2N), the organic layers separated, dried over magnesium sulfate and evaporated to dryness. The raw product was purified by column chromatography on silicagel using methylene chloride/methyl-tertbutyl ether (9/1) as eluent. Yield 1.0 g, m.p. 166° C.

The following examples 9–67 are examples of compounds useful according to the present invention which are commercially available from commercial sources like Specs, Maybridge, Bionet, and Salor.

| Compound | Example No. |
| --- | --- |
| 2-(2,5-Dimethyl-benzofuran-7-yl)-4H-3,1-benzoxazin-4-one | 9 |
| 2-(3-Bromo-phenyl)-4H-3,1-benzoxazin-4-one | 10 |
| 2-(3-Bromo-phenyl)-7-chloro-4H-3,1-benzoxazin-4-one | 11 |
| 2-(2,4-Dichloro-phenyl)-4H-3,1-benzoxazin-4-one | 12 |
| 2-m-Tolyl-4H-3,1-benzoxazin-4-one | 13 |
| 2-(2-Fluoro-phenyl)-6-methyl-3,1-benzoxazin-4-one | 14 |
| 2-(4-tert-Butyl-phenyl)-7-chloro-4H-3,1-benzoxazin-4-one | 15 |
| Naphthalene-2-sulfinic acid [2-(4-oxo-4H-3,1-benzoxazin-2-yl)-phenyl]-amide | 16 |
| 2-(4-Chloro-3-nitro-phenyl)-6,7-dimethoxy-4H-3,1-benzoxazin-4-one | 17 |
| 2-(5-Chloro-2-methoxy-phenyl)-4H-3,1-benzoxazin-4-one | 18 |
| 6-Bromo-2-(5-chloro-2-methoxy-phenyl)-4H-3,1-benzoxazin-4-one | 19 |
| 2-(3,4-Dichloro-phenyl)-6,7-dimethoxy-4H-3,1-benzoxazin-4-one | 20 |
| 2-(3,4-Dimethyl-phenyl)-4H-3,1-benzoxazin-4-one | 21 |
| 7-Chloro-2-(4-methyl-3-nitro-phenyl)-4H-3,1-benzoxazin-4-one | 22 |
| 6,7-Dimethoxy-2-p-tolyl-4H-3,1-benzoxazin-4-one | 23 |
| 2-phenyl-4H-3,1-benzoxazin-4-one | 24 |
| 6,7,8-Trimethoxy-2-(3-trifluoromethyl-phenyl)-4H-3,1-benzoxazin-4-one | 25 |
| 6,7-Dimethoxy-2-[2-(4-methoxy-phenoxy)-5-nitro-phenyl]-4H-3,1-benzoxazin-4-one | 26 |
| 5-Chloro-2-[2-(4-methoxy-phenoxy)-5-nitro-phenyl]-4H-3,1-benzoxazin-4-one | 27 |
| 2-(4-tert-Butyl-phenyl)-7-chloro-4H-3,1-benzoxazin-4-one | 28 |
| 7-Chloro-2-m-tolyl-4H-3,1-benzoxazin-4-one | 29 |
| 6,7-Dimethoxy-2-(5-methyl-2-nitro-phenyl)-4H-3,1-benzoxazin-4-one | 30 |
| 7-Chloro-2-(4-chloro-3-nitro-phenyl)-4H-3,1-benzoxazin-4-one | 31 |
| 2-(3,4-Dimethyl-phenyl)-6,7-dimethoxy-4H-3,1-benzoxazin-4-one | 32 |
| 7-Chloro-2-[4-(5-ethyl-pyridin-2-yl)-phenyl]-4H-3,1-benzoxazin-4-one | 33 |
| 2-(4-Chloro-3-nitrophenyl)-6,7,8-trimethoxy-4H-3,1-benzoxazin-4-one | 34 |
| 2-(2,6-Difluorophenyl)-5-fluoro-4H-3,1-benzoxazin-4-one | 35 |
| 2-(2-Fluorophenyl)-4H-3,1-benzoxazin-4-one | 36 |
| 5-Chloro-2-(3-trifluoromethylphenyl)-4H-3,1-benzoxazin-4-one | 37 |
| 2-(3,4-Dichloro-phenyl)-6-nitro-4H-3,1-benzoxazin-4-one | 38 |
| 2-(2-Chloro-6-fluorophenyl)-5-fluoro-3,1-benzoxazin-4-one. | 39 |
| 7-Chloro-2-(2-fluorophenyl)-3,1-benzoxazin-4-one | 40 |
| 2-(2-Chloro-6-fluorophenyl)-6-methyl-4H-3,1-benzoxazin-4-one | 41 |
| 2-(2-(4-Fluorophenylsulfonyl)amidophenyl)-4H-3,1-benzoxazin-4-one | 42 |
| 2-(2-Bromo-5-methoxy-phenyl)-4H-3,1-benzoxazin-4-one | 43 |
| 2-(2-Chloromethyl-phenyl)-4H-3,1-benzoxazin-4-one | 44 |
| 2-(4-tert-Butyl-phenyl)-6,8-dimethyl-4H-3,1-benzoxazin-4-one | 45 |
| 2-(2-Chloro-phenyl)-6-methyl-4H-3,1-benzoxazin-4-one | 46 |
| 7-Chloro-2-(3-chloromethyl-phenyl)-4H-3,1-benzoxazin-4-one | 47 |
| 2-(2-Chloro-phenyl)-6-iodo-4H-3,1-benzoxazin-4-one | 48 |
| 7-Chloro-2-(2-chloro-5-nitro-phenyl)-4H-3,1-benzoxazin-4-one | 49 |
| 2-(2-Bromo-phenyl)-6-chloro-4H-3,1-benzoxazin-4-one | 50 |
| 6,7-Dimethoxy-2-(3-nitro-phenyl)-4H-3,1-benzoxazin-4-one | 51 |
| 2-(3-Nitro-phenyl)-4H-3,1-benzoxazin-4-one | 52 |
| 7-chloro-2-(2,4-dichlorophenyl)-4H-3,1-benzoxazin-4-one | 53 |
| 2-(2,4-Dichloro-phenyl)-6-iodo-4H-3,1-benzoxazin-4-one | 54 |
| 6-Bromo-2-(3-chloro-5-trifluoromethyl-pyridin-2-yl)-4H-3,1-benzoxazin-4-one | 55 |
| 6-(6,7-Dimethoxy-4-oxo-4H-3,1-benzoxazin-2-yl)-pyridine-2-carboxylic acid methyl ester | 56 |
| 6,7-Dimethoxy-2-pyridin-4-yl-4H-3,1-benzoxazin-4-one | 57 |
| 6-Bromo-2-pyridin-4-yl-4H-3,1-benzoxazin-4-one | 58 |
| 5-Fluoro-2-(2-phenoxy-pyridin-3-yl)-4H-3,1-benzoxazin-4-one | 59 |
| 6,7,8-Trimethoxy-2-(2-phenoxy-pyridin-3-yl)-4H-3,1-benzoxazin-4-one | 60 |
| 2-(3-Chloro-5-trifluoromethyl-pyridin-2-yl)-6,7-dimethoxy-4H-3,1-benzoxazin-4-one | 61 |
| 2-Thiophen-2-yl-4H-3,1-benzoxazin-4-one | 62 |
| 6,7,8-Trimethoxy-2-(5-nitro-furan-2-yl)-4H-3,1-benzoxazin-4-one | 63 |
| 6-Methyl-2-(5-nitro-furan-2-yl)-4H-3,1-benzoxazin-4-one | 64 |
| 2-(2,4-Dichloro-phenyl)-6-nitro-benzo[d][1,3]oxazin-4-one | 65 |
| 6,8-Dibromo-2-(2-fluoro-phenyl)-benzo[d][1,3]oxazin-4-one | 66 |
| 7-Chloro-2-(2-chloromethyl-phenyl)-4H-3,1-benzoxazin-4-one | 67 |

The following examples 68–122 describ enovel compounds according to the invention. The compounds of examples 68–110 were prepared using solution phase parallel synthesis following the general description below:

The appropriately substituted 2-aminobenzoic acid (30 mg) was dissolved in toluene (300 uL), triethyl amine (300 uL) was added and the mixture shaken for 10 min at RT.

Appropriate substituted benzoic acid chloride (2.2 equivalent) was added and the mixture shaken overnight at RT (room temperature).

Ethyl acetate (1 mL) and HCl (0.1 N, 1 mL) were added followed by shaking for 30 min.

The organic layer was separated and added sat. NaHCO3 (0.5 mL) and the mixture shaken for 2 min. The organic layer was separated and filtered through a silicagel column (Sep-Pack plus), the column washed with dichloromethane (3 mL) and the collected organic phases evaporated.

The identity and purity was checked by LC-MS using an PE Sciex API 100 LC/MS system using Waters 3 mm×150 mm 3.5 u C-18 symmetry column and positive ion-spray with a flow rate at 20 uL/min.

The column was eluted with a linear gradient of 5–90% acetonitrile, 85–0% water and 10% trifluoroacetic acid (0.1%).

| Ex. | Compound | |
|---|---|---|
| 68 | 2-(2,6-Difluoro-phenyl)-6-methoxy-benzo[d][1,3]oxazin-4-one | m/z; 290 RT: 13,68/11,45 ELS; 80% |
| 69 | 2-(2-Fluoro-phenyl)-6-methoxy-benzo[d][1,3]oxazin-4-one | m/z: 272 RT: 14,10 ELS: 98% |
| 70 | 2-(2,6-Difluoro-phenyl)-7-trifluoromethyl-benzo[d][1,3]oxazin-4-one | m/z: 328 RT: 15,51 ELS: 91% |
| 71 | 6,7-Difluoro-2-(2-fluoro-phenyl)-benzo[d][1,3]oxazin-4-one | m/z: 278 RT: 14,78 ELS: 97% |
| 72 | 6,7-Difluoro-2-thiophen-2-yl-benzo[d][1,3]oxazin-4-one | m/z: 266 RT: 14,68 ELS: 98% |
| 73 | 6,7-Difluoro-2-furan-2-yl-benzo[d][1,3]oxazin-4-one | m/z: 250 RT: 12,88 ELS: 99% |
| 74 | 2-(2,6-Difluoro-phenyl)-4-oxo-4H-benzo[d][1,3]oxazine-5-carboxylic acid methyl ester | m/z: 318 RT: 12,82 ELS: 67% |
| 75 | 2-(2-Fluoro-phenyl)-4-oxo-4H-benzo[d][1,3]oxazine-5-carboxylic acid methyl ester | m/z: 300 RT: 12,97 ELS: 100% |
| 76 | 4-Oxo-2-thiophen-2-yl-4H-benzo[d][1,3]oxazine-5-carboxylic acid methyl ester | m/z: 288 RT: 12,97/10,07 |
| 77 | 2-Furan-2-yl-4-oxo-4H-benzo[d][1,3]oxazine-5-carboxylic acid methyl ester | m/z: 272 RT: 10,67 ELS: 84% |
| 78 | 2-(2-Methoxy-phenyl)-6-nitro-benzo[d][1,3]oxazin-4-one | m/z: 299 Rt: 13,48 ELS: 11% |
| 79 | 2-(2-Methoxy-phenyl)-5-methyl-benzo[d][1,3]oxazin-4-one | m/z: 268 Rt: 13,84 ELS: 35% |
| 80 | 2-(2-Methoxy-phenyl)-5-nitro-benzo[d][1,3]oxazin-4-one | m/z: 299 Rt: 12,81 ELS: 61% |
| 81 | 6-Nitro-2-(2-nitro-phenyl)-benzo[d][1,3]oxazin-4-one | m/z: 314 Rt: 13,48 ELS: 35% |
| 82 | 6-Nitro-2-o-tolyl-benzo[d][1,3]oxazin-4-one | m/z: 283 Rt: 14,11 ELS: 49% |
| 83 | 5-Nitro-2-(2-nitro-phenyl)-benzo[d][1,3]oxazin-4-one | m/z: 314 Rt: 13,11 ELS: 81% |
| 84 | 5-Nitro-2-(2-nitro-phenyl)-benzo[d][1,3]oxazin-4-one | m/z: 314 Rt: 12.88 ELS: 85% |
| 85 | 2-(2-Chloro-pyridin-3-yl)-6-nitro-benzo[d][1,3]oxazin-4-one | m/z: 304 Rt: 11,94 ELS: 88% |
| 86 | 2-(2-Chloro-pyridin-3-yl)-5-methyl-benzo[d][1,3]oxazin-4-one | m/z: 273 Rt: 12,61 ELS: 100% |
| 87 | 2-(2-Chloro-pyridin-3-yl)-5-nitro-benzo[d][1,3]oxazin-4-one | m/z: 304 Rt: 11,64 ELS: 82% |
| 88 | 2-(2,3-Difluoro-phenyl)-6-nitro-benzo[d][1,3]oxazin-4-one | m/z: 305 Rt: 14,26 ELS: 80% |
| 89 | 2-(2,3-Difluoro-phenyl)-5-methyl-benzo[d][1,3]oxazin-4-one | m/z: 274 Rt: 15,31 ELS: 82% |
| 90 | 2-(2,3-Difluoro-phenyl)-5-nitro-benzo[d][1,3]oxazin-4-one | m/z: 305 Rt: 13,70 ELS: 95% |
| 91 | Acetic acid 2-(6-nitro-4-oxo-4H-benzo[d][1,3]oxazin-2-yl)-phenyl ester | m/z: 327 Rt: 13,37 ELS: 54% |
| 92 | Acetic acid 2-(5-methyl-4-oxo-4H-benzo[d][1,3]oxazin-2-yl)-phenyl ester | m/z: 296 Rt: 14,11 ELS: 54% |
| 93 | Acetic acid 2-(5-nitro-4-oxo-4H-benzo[d][1,3]oxazin-2-yl)-phenyl ester | m/z: 327 Rt: 12,88 ELS: 84% |
| 94 | 2-(2,6-Difluoro-phenyl)-6-trifluoromethyl-benzo[d][1,3]oxazin-4-one | m/z: 328 Rt: 15,26 ELS: 82% |
| 95 | 2-(2-Fluoro-phenyl)-6-trifluoromethyl-benzo[d][1,3]oxazin-4-one | m/z: 310 Rt: 91 ELS: 91% |
| 96 | 2-Thiophen-2-yl-6-trifluoromethyl-benzo[d][1,3]oxazin-4-one | m/z: 298 Rt: 15,42 ELS: 100% |
| 97 | 2-(2,6-Difluoro-phenyl)-5-trifluoromethyl-benzo[d][1,3]oxazin-4-one | m/z: 328 Rt: 15,72 ELS: 79% |
| 98 | 2-(2-Fluoro-phenyl)-5-trifluoromethyl-benzo[d][1,3]oxazin-4-one | m/z: 310 Rt: 15,47 ELS: 81% |
| 99 | 2-Thiophen-2-yl-5-trifluoromethyl-benzo[d][1,3]oxazin-4-one | m/z: 298 Rt: 14,95 ELS: 56% |
| 100 | 2-(2,6-Difluoro-phenyl)-8-trifluoromethyl-benzo[d][1,3]oxazin-4-one | m/z: 328 Rt: 14,73 ELS: 94% |
| 101 | 2-(2-Fluoro-phenyl)-8-trifluoromethyl-benzo[d][1,3]oxazin-4-one | m/z: 310 Rt: 15,15 ELS: 99% |
| 102 | 2-Furan-2-yl-8-trifluoromethyl-benzo[d][1,3]oxazin-4-one | m/z: 282 Rt: 13,88 ELS: 80% |
| 103 | 2-(2-Fluoro-phenyl)-4-oxo-4H-benzo[d][1,3]oxazine-5-carboxylic acid ethyl ester | m/z: 314 Rt: 13,73 ELS: 95% |
| 104 | 2-(2,6-Difluoro-phenyl)-7-fluoro-benzo[d][1,3]oxazin-4-one | m/z 278 Rt: 13,47 ELS: 90% |
| 105 | 5-Nitro-2-(5-nitro-furan-2-yl)-benzo[d][1,3]oxazin-4-one | m/z: 304 Rt: 11.84 ELS: 90% |
| 106 | 2-(2,3-Dichloro-phenyl)-6,7-difluoro-benzo[d][1,3]oxazin-4-one | m/z: 328 Rt.: 16,15 ELS: 100% |
| 107 | 6,7-Difluoro-2-(2-trifluoromethoxy-phenyl)-benzo[d][1,3]oxazin-4-one | m/z: 344 Rt.: 16,05 ELS: 92% |

-continued

| Ex. | Compound | | |
|---|---|---|---|
| 108 | 2-(2,3-Difluoro-phenyl)-6,7-difluoro-benzo[d][1,3]oxazin-4-one | m/z: 296 | Rt: 14,91 ELS: 98% |
| 109 | 6,7-Difluoro-2-(2-methoxy-phenyl)-benzo[d][1,3]oxazin-4-one | m/z: 290 | Rt: 14,09 |
| 110 | 2-(2-Chloro-pyridin-3-yl)-6,7-difluoro-benzo[d][1,3]oxazin-4-one | m/z: 295 | Rt: 12,75 ELS: 96% | m/z: The molecular ion (M + 1) from the LC-MS investigation.
RT: Retention time
ELS: The purity estimated from the electrospray (positive ion) measurement.

Example 111
2-(2,6-Difluoro-phenyl)-6-nitro-benzo[d][1,3]oxazin-4-one (9).

5-Nitroanthranilic acid (0.6 g) was dissolved in triethyl amine/toluene (1/1) (18 mL) and stirred for 10 min. 2,6-Difluorobenzoylchloride (1.3 g) was slowly added under stirring which resulted in the formation of a precipitate. The reaction was performed in an N2-atmosphere. After stirring at RT for 24 h the mixture was extracted with sat.NaHCO3 and ethyl acetate (20 mL), the organic layer was separated and evaporated.

The crude product was rinsed by precipitation from hot dioxane, the resulting mass transferred to a silicagel cloumn and eluted with dichloromethane, the isolated fraction was dissolved in hot toluene (2 mL) and precipitated with hexane, resulting in 2-(2,6-difluorophenyl)-6-nitro-benzo[d][1,3]oxazin-4-one (0.13 g), mp. 188 C, MS m/e.: 304 (M+).

Example 112
6-Acetamido-(2,6-difluoro-phenyl)-benzo[d][1,3]oxazin-4-one (10), 5-Acetamidoanthranilic acid (0.64g) and 2,6-difluorobenzoyl chloride (1.3 g) were reacted in triethyl amine/toluene (1/1) (20 mL) like described for compound (9), reaction time 1 h. Ethyl acetate (50 mL) and HCl-solution (1 mL 4N in 50 mL water) were added resulting in the formation of a precipitate.The mixture was filtered and the residue dissolved in THF followed by evaporation to dryness, subsequent dissolution in hot dioxane followed by precipitation with hexane resulted in colourless crystals of 6-acetamido-(2,6-difluoro-phenyl)-benzo[d][1,3]oxazin-4-one (0.98 g), mp.246 C, MS m/e.: 316 M+.

Example 113
2-(2,6-Difluoro-phenyl)-5-methyl-benzo[d][1,3]oxazin-4-one (11).

2-Amino-6-methylbenzoic acid (0.498 g), 2,6-difluorobenzoyl chloride (0.93 mL) and triethyl amine/toluene (1/1) (20 mL) were reacted as described under (10).

Extraction between ethyl acetate (100 mL) and HCl (2N, 100 mL), followed by separation of the organic layer, drylng over MgSO4, filtering and evaporation gave a crude product which was re-dissolved in toluene(10 mL) and precipitated with hexane (5 mL) resulting in 2-(2,6-difluoro-phenyl)-5-methyl-benzo[d][1,3]oxazin-4-one (0.45 g). m.p. 156 C, MS. m/e: 273 M+.

Example 114
2-(2,6-Difluoro-phenyl)-7-nitro-benzo[d][1,3]oxazin-4-one (12).

4-Nitroanthranilic acid (0.6 g), 2,6-difluorobenzoyl chloride (0.93 mL) and triethyl amine/toluene (1/1) (18 mL) were reacted as described under (10). reaction time 2 days. Extraction between ethyl acetate (100 mL) and HCl (2N, 100 mL), followed by separation of the organic layer, drylng over MgSO4, filtering and evaporation gave a crude product which was dissolved in warm THF (20 mL) and precipitated with hexane twice to get the pure product 2-(2,6-difluoro-phenyl)-7-nitro-benzo[d][1,3]oxazin-4-one (0.417 g), mp. 187 C, MS m/e: 304 M+.

Example 115
2-(2,6-Difluoro-phenyl)-5-nitro-benzo[d][1,3]oxazin-4-one (13),

6-Nitroanthranilic acid (0.6 g), 2,6-difluorobenzoyl chloride (0.93 mL) and triethyl amine/toluene (1/1) (18 mL) were reacted as described under (10). Reaction time 2 days. Extraction between ethyl acetate (100 mL) and HCl (2N, 100 mL), followed by separation of the organic layer, drylng over MgSO4, filtering and evaporation gave a crude product which was dissolved in warm THF (20 mL) and precipitated with hexane. The resulting mixture was further purified on a silicagel column using dichloromethane as eluent. The isolated fraction was dissolved in warm THF (20 mL) and precipitated with hexane, ylelding 2-(2,6-difluoro-phenyl)-5-nitro-benzo[d][1,3]oxazin-4-one (0.475 g) mp. 172 C, MS m/e: 304 M+, LC-MS m/e 305 (M+1) ELS purity 100%.

Example 116
5-Chloro-2-(2,6-difluoro-phenyl)-benzo[d][1,3]oxazin-4-one (14).

6-Chloroanthranilic acid (0.566 g), 2,6-difluorobenzoyl chloride (0.93 mL) and triethyl amine/toluene (1/1) (18 mL) were reacted as described under (10). Reaction time 2 days. Extraction between ethyl acetate (100 mL) and HCl (2N, 100 mL), followed by separation of the organic layer, drylng over MgSO4, filtering and evaporation gave a crude product which was dissolved in warm THF (20 mL) and precipitated with hexane. The resulting mixture was further purified on a silicagel column using dichloromethane as eluent. The isolated fraction was dissolved in warm THF (20 mL) and precipitated with hexane, ylelding 5-chloro-2-(2,6-difluoro-phenyl)-benzo[d][1,3]oxazin-4-one (0.65 g) mp. 176 C, MS m/e: 293/295 M+.

Example 117
6-Amino-2-(2,6-difluoro-phenyl)-benzo[d][1,3]oxazin-4-one (15).

6-Nitro-2-(2,6-difluoro-phenyl)-benzo[d][1,3]oxazin-4-one (50 mg) was dissolved in acetic acid (5 mL) under N2, PtO2 (2.5 mg) was added and the mixture was hydrogenated with H2 gas. Reaction time 2 h. The reaction mixture was filtered through Hyflo®, which was rinsed afterwards with ethyl acetate. The combined organic phases were evaporated to dryness and subsequently treated three times with toluene followed by evaporation.

The resulting mixture was dissolved in THF and precipitated with hexane resulting in 6-amino-2-(2,6-difluorophenyl)-benzo[d][1,3]oxazin-4-one (12 mg), LC-MS 275 M+1, ELS purity 96%.

Example 118
2-(2,6-Difluoro-phenyl)-8-hydroxy-benzo[d][1,3]oxazin-4-one (16).

3-Triisopropylsilyloxyanthranilic acid (0.8 g), 2,6-difluorobenzoyl chloride (0.71 mL) and triethyl amine/toluene (1/1) (25 mL) were reacted as described under (10). Reaction time 2 days. Extraction between ethyl acetate (100 mL) and HCl (1N,100 mL), followed by separation of the organic layer, drylng over MgSO4, filtering and evaporation gave a crude product which was dissolved in warm THF (20 mL) and precipitated with hexane. The resulting mixture was further purified on a silicagel column using dichloromethane as eluent. The isolated fraction (80 mg) was hydrolysed with 1% HCl in ethanol by stirring for 2 days at RT, and further hydrolysis after addition of HCl (4N, 5 mL) and ethyl acetate (10 mL). The organic layer was separated, evaporated and dried resulting in 2-(2,6-difluoro-phenyl)-8-hydroxy-benzo[d][1,3]oxazin-4-one (32 mg), mp.190–198. LC-MS showed the purity 86% with the corresponding O-triisopropylsilylated product as the impurity.

Example 119
5,8-Dichloro-2-(2,6-difluoro-phenyl)-benzo[d][1,3]oxazin-4-one (17), 2-Amino-3,6-dichlorobenzoic acid (0.125 g), 2,6-difluorobenzoyl chloride (0.168 mL) and triethyl amine/toluene (1/1) (1,5 mL) were reacted by heating to 50° C. for 2 h. HCL (0.2 N, 1 mL) was added and the organic layer separated and rinsed by pressing through a silicagel column (Sep Pack).

Evaporation resulted in the isolation of 5,8-dichloro-2-(2,6-difluoro-phenyl)-benzo[d][1,3]oxazin-4-one (0.20 g), mp. 190 C, MS m/e: 328 M+. LC-MS-purity 99,1%.

Example 120
5-Amino-2-(2,6-difluoro-phenyl)-benzo[d][1,3]oxazin-4-one (18).

5-Nitro-2-(2,6-difluoro-phenyl)-benzo[d][1,3]oxazin-4-one (0.4 g) was dissolved in acetic acid (30 mL) under N2, PtO2 (20 mg) was added and the mixture was hydrogenated with H2 gas. Reaction time 1 day. The reaction mixture was filtered through Hyflo®, which was rinsed afterwards with ethyl acetate. The combined organic phases were evaporated to dryness and subsequently treated three times with toluene followed by evaporation. The resulting mixture was dissolved in THF and precipitated with hexane giving a crude product which was purified on a silicagel column using dichloromethane as eluent. One fraction was collected (51 mg), identified as 5-amino-2-(2,6-difluoro-phenyl)-benzo[d][1,3]oxazin-4-one, LC-MS 275 M+1, ELS purity 100%, mp. 197 C.

Example 121
2-(2,6-Difluoro-phenyl)-6,7-difluoro-benzo[d][1,3]oxazin-4-one (19).

2-Amino-4,5-difluorobenzoic acid (0.5 g), 2,6-difluorobenzoyl chloride (0.80 mL) and triethyl amine/toluene (1/1) (18 mL) were reacted as described under (10). Reaction time 1 day. Extraction between ethyl acetate (20 mL) and HCl (2N,20 mL), followed by separation of the organic toluene and precipitated with hexane. The resulting mixture was further purified on a silicagel column using dichloromethane as eluent. The isolated fraction identified as 2-(2,6-difluoro-phenyl)-6,7-difluoro-benzo[d][1,3]oxazin-4-one (0.71 g), mp. 165 C, MS m/e: 295 M+.

Example 122
7-Amino-2-(2,6-difluoro-phenyl)-benzo[d][1,3]oxazin-4-one (20)

7-Nitro-2-(2,6-difluoro-phenyl)-benzo[d][1,3]oxazin-4-one (0.10 g) was dissolved in acetic acid (10 mL) under N2, PtO2 (5 mg) was added and the mixture was hydrogenated with H2 gas. Reaction time 1 day. The reaction mixture was filtered through Hyflo®, which was rinsed afterwards with ethyl acetate. The combined organic phases were evaporated to dryness and subsequently treated three times with toluene followed by evaporation.

The resulting mixture was purified on a silicagel column using dichloromethane as eluent. One fraction was collected (15 mg), identified as 7-amino-2-(2,6-difluoro-phenyl)-benzo[d][1,3]oxazin-4-one, LC-MS 275 M+1, mp. 196 C.

Example 123

| Compound | Example No. | IC50 TF/FVII/FX μM |
|---|---|---|
| 2-(2-Fluoro-phenyl)-4-oxo-4H-benzo[d][1,3]-oxazine-5-carboxylic acid methyl ester | 75 | 5.6 |
| 2-(2-Fluoro-phenyl)-6-trifluoromethyl-benzo[d][1,3]oxazin-4-one | 95 | 3.1 |
| 2-(2-Chloro-pyridin-3-yl)-5-nitro-benzo[d][1,3]oxazin-4-one | 87 | 2.8 |
| 2-(2-Bromo-5-methoxy-phenyl)-4H-3,1-benzoxazin-4-one | 43 | 1.1 |
| 2-(2-Chloro-6-fluorophenyl)-6-methyl-4H-3,1-benzoxazin-4-one | 41 | 0.9 |
| 2-m-Tolyl-4H-3,1-benzoxazin-4-one | 13 | 0.6 |
| 5-Nitro-2-(2-nitro-phenyl)-benzo[d][1,3]-oxazin-4-one | 83 and 84 | 0.32 |
| 5-Chloro-2-(2,6-difluoro-phenyl)-benzo[d][1,3]oxazin-4-one | 116 | 0.17 |

IC50 TF/FVII/FX: The IC50 value in μM found from the FX activation assay described above.

Example 124

| Compound | Example No. | Clot Ratio % |
|---|---|---|
| 2-(2,6-Dichloro-phenyl)-6-methyl-4H-3,1-benzoxazin-4-one | 3 | 1.88 |
| 6,7-Difluoro-2-(2-fluoro-phenyl)-benzo[d][1,3]oxazin-4-one | 71 | 1.6 |
| 6-Amino-2-(2,6-difluoro-phenyl)-benzo[d][1,3]oxazin-4-one | 117 | >30 |
| 2-(2-Bromo-5-methoxy-phenyl)-4H-3,1-benzoxazin-4-one | 43 | >30 |
| 2-(2,6-Difluoro-phenyl)-6-methoxy-benzo[d][1,3]oxazin-4-one | 68 | 2.3 |
| 2-(2-Chloro-pyridin-3-yl)-6,7-difluoro-benzo[d][1,3]oxazin-4-one | 110 | 2.3 |
| 2-(2,6-Difluoro-phenyl)-6,7-difluoro-benzo[d][1,3]oxazin-4-one | 121 | 3.0 |

Clot Ratio %: The clot ratio found in the clotting assay described above.

What is claimed is:

1. A method of modulating and normalizing an impaired haemostatic balance in a mammal, which method comprises administering an effective amount of a compound with formula I:

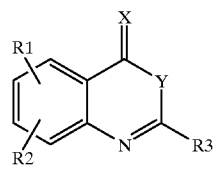

(I)

wherein

X is O, S or NH;

Y is O;

$R^1$ and $R^2$ independently are $C_{1-8}$-alkyl, $C_{2-8}$ alkenyl, $C_{2-8}$ alkynyl, or $C_{3-6}$ cycloalkyl, each optionally substituted with halogen, OH, $NH_2$, $NHR^4$, $N(R^4)_2$, $NHCOR^4$, $C_{1-4}$ alkoxy, trifluoromethoxy, carbamoyl, $CONHR^4$, or $CON(R^4)_2$); H, Halogen, $C_{1-6}$ alkoxy, $C_{1-6}$ alkylthio, $OCF_3$, COOH, CN, $CONH_2$, $CONHR^4$, OH, $NH_2$, $NHR^4$, $N(R^4)_2$, $NHCOR^4$, $CON(R^4)_2$, $CONHSO_2R^4$, $SO_2NH_2$, $SO_2NHR^4$, $C_{1-4}$ alkoxycarbonyl, phenyl, alkylphenyl, or tetrazole $R^3$ is aryl or heteroaryl selected from the group consisting of phenyl, biphenyl, indenyl, fluorenyl, naphthyl, anthracenyl, thienyl, furyl, indolyl, oxadiazolyl, isoxazolyl, quinazolinyl, xanthenyl, isoindanyl, benzhydryl, acridinyl, pyrazolyl, triazolyl, oxazolyl, pyrimidinyl, pyrazinyl, pyridazinyl, benzo[b]furanyl, 2,3-dihydrobenzo[b]furanyl, benzo[b]thiophenyl, 2,3-dihydro-benzo[b]thiophenyl, indazolyl, benzimidazolyl, benzoxazolyl, benzothiazolyl, carbazolyl, 5H-dibenzo[b,f]azepine, and 10,11-dihydro-5H-dibenz[b,f]azepine, each optionally substituted with one or more $C_{1-8}$-alkyl, $C_{2-8}$ alkenyl, $C_{2-8}$ alkynyl, or $C_{3-8}$ cycloalkyl, each optionally substituted with halogen, OH, $NH_2$, $NHR^4$, $N(R^4)_2$, $NHCOR^4$, $C_{1-4}$ alkoxy, trifluoromethoxy, carbamoyl, $CONHR^4$, or $CON(R^4)_2$; Halogen, $C_{1-6}$ alkoxy, $C_{1-6}$ alkylthio, $OCF_3$, COOH, CN, $CONH_2$, $CONHR^4$, OH, $NH_2$, $NHR^4$, $N(R^4)_2$, $NHCOR^4$, $CON(R^4)_2$, $CONHSO_2R^4$, $SO_2NH_2$, $SO_2NHR^4$, $C_{1-4}$ alkoxycarbonyl, phenyl, alkylphenyl, or tetrazole;

$R^4$ is $C_{1-4}$-alkyl, $C_{2-4}$ alkenyl, $C_{2-4}$ alkynyl, $C_{3-6}$ cycloalkyl, or phenyl;

or pharmaceutically acceptable salts thereof, in combination with a pharmaceutically acceptable excipient and/or carrier to the mammal in need thereof.

2. The method of claim 1, wherein X is O, and Y is O.

3. The method of claim 1, wherein X is S, and Y is O.

4. The method of claim 1, wherein X is NH, and Y is O.

5. A method for treatment of coagulation-related diseased states in a mammal, wherein the method comprises administering an effective amount of a compound with formula I:

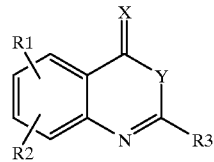

(I)

wherein

X is O, S or NH;

Y is O;

$R^1$ and $R^2$ independently are $C_{1-8}$-alkyl, $C_{2-8}$ alkenyl, $C_{2-8}$ alkynyl, or $C_{3-6}$ cycloalkyl, each optionally substituted with halogen, OH, $NH_2$, $NHR^4$, $N(R^4)_2$, $NHCOR^4$, $C_{1-4}$ alkoxy, trifluoromethoxy, carbamoyl, $CONHR^4$, or $CON(R^4)_2$); H, Halogen, $C_{1-6}$ alkoxy, $C_{1-6}$ alkylthio, $OCF_3$, COOH, CN, $CONH_2$, $CONHR^4$, OH, $NH_2$, $NHR^4$, $N(R^4)_2$, $NHCOR^4$, $CON(R^4)_2$, $CONHSO_2R^4$, $SO_2NH_2$, $SO_2NHR^4$, $C_{1-4}$ alkoxycarbonyl, phenyl, alkylphenyl, or tetrazole $R^3$ is aryl or heteroaryl selected from the group consisting of phenyl, biphenyl, indenyl, fluorenyl, naphthyl, anthracenyl, thienyl, furyl, indolyl, oxadiazolyl, isoxazolyl, quinazolinyl, xanthenyl, isoindanyl, benzhydryl, acridinyl, pyrazolyl, triazolyl, oxazolyl, pynmidinyl, pyrazinyl, pyridazinyl, benzo[b]furanyl, 2,3-dihydrobenzo[b]furanyl, benzo[b]thiophenyl, 2,3-dihydro-benzo[b]thiophenyl, indazolyl, benzimidazolyl, benzoxazolyl, benzothiazolyl, carbazolyl, 5H-dibenz[b,f]azepine, and 10,11-dihydro-5H-dibenz[b,f]azepine, each optionally substituted with one or more $C_{1-8}$-alkyl, $C_{2-8}$ alkenyl, $C_{2-8}$ alkynyl, or $C_{3-6}$ cycloalkyl, each optionally substituted with halogen, OH, $NH_2$, $NHR^4$, $N(R^4)_2$, $NHCOR^4$, $C_{1-4}$ alkoxy, trifluoromethoxy, carbamoyl, $CONHR^4$, or $CON(R^4)_2$; Halogen, $C_{1-6}$ alkoxy, $C_{1-6}$ alkylthio, $OCF_3$, COOH, CN, $CONH_2$, $CONHR^4$, OH, $NH_2$, $NHR^4$, $N(R^4)_2$, $NHCOR^4$, $CON(R^4)_2$, $CONHSO_2R^4$, $SO_2NH_2$, $SO_2NHR^4$, $C_{1-4}$alkoxycarbonyl, phenyl, alkylphenyl, or tetrazole $R^4$ is $C_{1-4}$-alkyl, $C_{2-4}$ alkenyl, $C_{2-4}$ alkynyl, $C_{3-6}$ cycloalkyl, or phenyl;

or pharmaceutically acceptable salts thereof, in combination with a pharmaceutically acceptable excipient and/or carrier to the mammal in need of such a treatment.

6. The method of claim 5, wherein the compound of formula I is an inhibitor of blood coagulation, or is an inhibitor of clotting activity, or is an inhibitor of deposition of fibrin, or is an inhibitor of platelet deposition.

7. The method of claim 5, for treatment of mammals suffering from deep vein thrombosis, pulmonary embolism, stroke, disseminated intravascular coagulation (DIC), vascular restenosis, platelet deposition and associated disorders and myocardial infarction, and in the prophylactic treatment of mammals with atherosclerotic vessels at risk for thrombosis.

8. A method for inhibiting tissue factor activity in a mammal which method comprises administering an effective amount of a compound with formula I

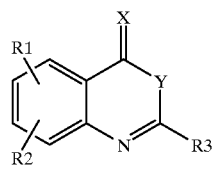

(I)

wherein

X is O, S or NH;

Y is O;

$R^1$ and $R^2$ independently are $C_{1-8}$-alkyl, $C_{2-8}$ alkenyl, $C_{2-8}$ alkynyl, or $C_{3-6}$ cycloalkyl, each optionally substituted with halogen, OH, $NH_2$, $NHR^4$, $N(R^4)_2$, $NHCOR^4$, $C_{1-4}$ alkoxy, trifluoromethoxy, carbamoyl, CONHR$^4$, or CON(R$^4$)$_2$); H, Halogen, alkoxy, C$_{1-6}$ alkylthio, OCF$_3$, COOH, CN, CONH$_2$, CONHR$^4$, OH, NH$_2$, NHR$^4$, N(R$^4$)$_2$, NHCOR$^4$, CON(R$^4$)$_2$, CONHSO$_2$R$^4$, SO$_2$NH$_2$, SO$_2$NHR$^4$, C$_{1-4}$ alkoxycarbonyl, phenyl, alkylphenyl, or tetrazole R$^3$ is aryl or heteroaryl selected from the group consisting of phenyl, biphenyl, indenyl fluorenyl, naphthyl, anthracenyl, thienyl, furyl, indolyl, oxadiazolyl, isoxazolyl, quinazolinyl, xanthenyl, isoindanyl, benzhydryl, acridinyl, pyrazolyl, triazolyl, oxazolyl, pyrimidinyl, pyrazinyl, pyridazinyl, benzo[b]furanyl, 2,3-dihydrobenzo[b]furanyl, benzo[b]thiophenyl, 2,3-dihydro-benzo[b]thiophenyl, indazolyl, benzimidazolyl, benzoxazolyl, benzothiazolyl, carbazolyl, 5H-dibenzo[b,f]azepine, and 10,11-dihydro-5H-dibenz[b,f]azepine, each optionally substituted with one or more C$_{1-8}$-alkyl, C$_{2-8}$ alkenyl, C$_{2-8}$ alkynyl, or C$_{3-6}$ cycloalkyl, each optionally substituted with halogen, OH, NH$_2$, NHR$^4$, N(R$^4$)$_2$, NHCOR$^4$, C$_{1-4}$ alkoxy, trifluoromethoxy, carbamoyl, CONHR$^4$, or CON(R$^4$)$_2$; Halogen, C$_{1-6}$ alkoxy, C$_{1-6}$ alkylthio, OCF$_3$, COOH, CN, CONH$_2$, CONHR$^4$, OH, NH$_2$, NHR$^4$, N(R$^4$)$_2$, NHCOR$^4$, CON(R$^4$)$_2$, CONHSO$_2$R$^4$, SO$_2$NH$_2$, SO$_2$NHR$^4$, C$_{1-4}$ alkoxycarbonyl, phenyl, alkylphenyl, or tetrazole R$^4$ is C$_{1-4}$-alkyl, C$_{2-4}$ alkenyl, C$_{2-4}$ alkynyl, C$_{3-6}$ cycloalkyl, or phenyl;

or pharmaceutically acceptable salts thereof, in combination with a pharmaceutically acceptable excipient and/or carrier to the mammal in need thereof.

9. A method for inhibiting factor VII activity by substantially reducing the ability of activated factor VII to catalyze tissue factor-enhanced activation of factors X and IX comprising administering a compound with formula I,

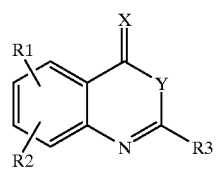

(I)

wherein

X is O, S, or NH;

Y is O;

R$^1$ and R$^2$ independently are

C$_{1-8}$-alkyl, C$_{2-8}$ alkenyl, C$_{2-8}$ alkynyl, or C$_{3-6}$ cycloalkyl, each optionally substituted with halogen, OH, NH$_2$, NHR$^4$, N(R$^4$)$_2$, NHCOR$^4$, C$_{1-4}$ alkoxy, trifluoromethoxy, carbamoyl, CONHR$^4$, or CON(R$^4$)$_2$); H, Halogen, C$_{1-6}$ alkoxy, C$_{1-6}$ alkylthio, OCF$_3$, COOH, CN, CONH$_2$, CONHR$^4$, OH, NH$_2$, NHR$^4$, N(R$^4$)$_2$, NHCOR$^4$, CON(R$^4$)$_2$, CONHSO$_2$R$^4$, SO$_2$NH$_2$, SO$_2$NHR$^4$, C$_{1-4}$ alkoxycarbonyl, phenyl, alkylphenyl, or tetrazole R$^3$ is aryl or heteroaryl selected from the group consisting of phenyl, biphenyl, indenyl, fluorenyl, naphthyl, anthracenyl, thienyl, furyl, indolyl, oxadiazolyl, isoxazolyl, quinazolinyl, xanthenyl, isoindanyl, benzhydryl, acridinyl, pyrazolyl, triazolyl, oxazolyl, pyrimidinyl, pyrazinyl, pyridazinyl, benzo[b]furanyl, 2,3-dihydrobenzo[b]furanyl, benzo[b]thiophenyl, 2,3-dihydro-benzo[b]thiophenyl, indazolyl, benzimidazolyl, benzoxazolyl, benzothiazolyl, carbazolyl, 5H-dibenz[b,f]azepine, and 10,11-dihydro-5H-dibenz[b,f]azepine, each optionally substituted with one or more C$_{1-8}$-alkyl, C$_{2-8}$ alkenyl, C$_{2-8}$ alkynyl, or C$_{3-8}$ cycloalkyl, each optionally substituted with halogen, OH, NH$_2$, NHR$^4$, N(R$^4$)$_2$, NHCOR$^4$, C$_{1-4}$ alkoxy, trifluoromethoxy, carbamoyl, CONHR$^4$, or CON(R$^4$)$_2$; Halogen, C$_{1-6}$ alkoxy, C$_{1-6}$ alkylthio, OCF$_3$, COOH, CN, CONH$_2$, CONHR$^4$, OH, NH$_2$, NHR$^4$, N(R$^4$)$_2$, NHCOR$^4$, CON(R$^4$)$_2$, CONHSO$_2$R$^4$, SO$_2$NH$_2$, SO$_2$NHR$^4$, C$_{1-4}$ alkoxycarbonyl, phenyl, alkylphenyl, or tetrazole R$^4$ is C$_{1-4}$-alkyl, C$_{2-4}$ alkenyl, C$_{2-4}$ alkynyl, C$_{3-6}$ cycloalkyl, or phenyl;

or pharmaceutically acceptable salts thereof, in combination with a pharmaceuticaliy acceptable excipient and/or carrier to a mammal in need of such treatment.

10. The method of claim 9, wherein the compound of formula I is selected from 2-(2,5-Dimethyl-benzofuran-7-yl)-4H-3,1-benzoxazin-4-one, 2-(3-Bromo-phenyl)-4H-3,1-benzoxazin-4-one, 2-(3-Bromo-phenyl)-7-chloro-4H-3,1-benzoxazin-4-one, 2-(2,4-Dichloro-phenyl)-4H-3,1-benzoxazin-4-one, 2-m-Tolyl-4H-3,1-benzoxazin-4-one, 2-(2-Fluoro-phenyl)-6-methyl-3,1-benzoxazin-4-one, 2-(4-tert-Butyl-phenyl)-7-chloro-4H-3,1-benzoxazin-4-one, Naphthalene-2-sulfinic acid [2-(4-oxo-4H-3,1-benzoxazin-2-yl)-phenyl]-amide, 2-(4-Chloro-3-nitro-phenyl)-6,7-dimethoxy-4H-3,1-benzoxazin-4-one, 2-(5-Chloro-2-methoxy-phenyl)-4H-3,1-benzoxazin-4-one, 6-Bromo-2-(5-chloro-2-methoxy-phenyl)-4H-3,1-benzoxazin-4-one, 2-(3,4-Dichloro-phenyl)-6,7-dimethoxy-4H-3,1-benzoxazin-4-one, 2-(3,4-Dimethyl-phenyl)-4H-3,1-benzoxazin-4-one, 7-Chloro-2-(4-methyl-3-nitro-phenyl)-4H-3,1-benzoxazin-4-one, 6,7-Dimethoxy-2-p-tolyl-4H-3,1-benzoxazin-4-one, 2-phenyl-4H-3,1-benzoxazin-4-one, 6,7,8-Trimethoxy-2-(3-trifluoromethyl-phenyl)-4H-3,1-benzoxazin-4-one, 6,7-Dimethoxy-2-[2-(4-methoxy-phenoxy)-5-nitro-phenyl]4H-3,1-benzoxazin-4-one, 5-Chloro-2-[2-(4-methoxy-phenoxy)-5-nitro-phenyl]-4H-3,1-benzoxazin-4-one, 2-(4-tert-Butyl-phenyl)-7-chloro-4H-3,1-benzoxazin-4-one, 7-Chloro-2-m-tolyl-4H-3,1-benzoxazinone-4-one, 6,7-Dimethoxy-2-(5-methyl-2-nitro-phenyl)-4H-3,1-benzoxazin-4-one, 7-Chloro-2-(4-chloro-3-nitro-phenyl)-4H-3,1-benzoxazin-4-one, 2-(3,4-Dimethyl-phenyl)-6,7-dimethoxy-4H-3,1-benzoxazin-4-one, 2-(4-Chloro-3-nitrophenyl)-6,7,8-trimethoxy-4H-3,1-benzoxazin-4-one, 2-(2,6-Difluorophenyl)-5-fluoro-4H-3,1-benzoxazin-4-one, 2-(2-Fluorophenyl)-4H-3,1-benzoxazin-4-one,
5-Chloro-2-(3-trifluoromethylphenyl)-4H-3,1-benzoxazin-4-one,
2-(3,4-Dichloro-phenyl)-6-nitro-4H-3,1-benzoxazin-4-one,
2-(-Chloro-6-fluorophenyl)-5-fluoro-3,1-benzoxazin-4-one,
7-Chloro-2-(2-fluorophenyl)-3,1-benzoxazin-4-one,
2-(2-Chloro-6-fluorophenyl)-6-methyl-4H-3,1-benzoxazin-4-one,
2(2-(4-Fluorophenylsulfonyl)amidophenyl)-4H-3,1-benzoxazin-4-one,
2-(2-Bromo-5-methoxy-phenyl)-4H-3,1-benzoxazin-4-one,
2-(2-Chloromethyl-phenyl)-4H-3,1-benzoxazin-4-one,
2-(4-tert-Butyl-phenyl)-6,8-dimethyl-4H-3,1-benzoxazin-4-one,
2-(2-Chloro-phenyl)-6-methyl-4H-3,1-benzoxazin-4-one,
7-Chloro-2-(3-chloromethyl-phenyl)-4H-3,1-benzoxazin-4-one,
2-(2-Chloro-phenyl)-6-iodo-4H-3,1-benzoxazin-4-one,
7-Chloro-2-(2-chloro-5-nitro-phenyl)-4H-3,1-benzoxazin-4-one,
2-(2-Bromo-phenyl)-6-chloro-4H-3,1-benzoxazin-4-one,
6,7-Dimethoxy-2-(3-nitro-phenyl)-4H-3,1-benzoxazin-4-one,
2-(3-Nitro-phenyl)-4H-3,1-benzoxazin-4-one,
7-chloro-2-(2,4-dichlorophenyl)-4H-3,1-benzoxazin-4-one,
2-(2,4-Dichloro-phenyl)-6-iodo-4H-3,1-benzoxazin-4-one,
2-Thiophen-2-yl-4H-3,1-benzoxazin-4-one,
6,7,8-Trimethoxy-2-(5-nitro-furan-2-yl)-4H-3,1-benzoxazin-4-one,
6-Methyl-2-(5-nitro-furan-2-yl)-4H-3,1-benzoxazin-4-one,
2-(2,4-Dichloro-phenyl)-6-nitro-benzo[d][1,3oxazin-4-one),
6,8-Dibromo-2-(2-fluoro-phenyl)-benzo[d][1,3]oxazin-4-one,
7-Chloro-2-(2-chloromethyl-phenyl)-4H-3,1-benzoxazin-4-one,
or pharmaceutical acceptable salts thereof.

11. A benzoxazin-4-one derivative selected from
5,8-Dichloro-2-(2-fluoro-phenyl)-4H-3,1-benzoxazin-4-one
6-Methyl-2-thiophen-2-yl-4H-3,1-benzoxazin-4-one
(2,6-Dichloro-phenyl)-6-methyl-4H-3,1-benzoxazin-4-one
6-Methyl-2-(2-trifluoromethoxy-phenyl)-4H-3,1-benzoxazin-4-one
(2,6-Difluoro-phenyl)-6-methyl-4H-3,1-benzoxazin-4-one
(2,6-Dimethoxy-phenyl)-6-methyl-4H-3,1-]benzoxazin-4-one
(3-Bromo-thiophen-2-yl)-6-methyl-4H-3,1-benzoxazin-4-one
(2,3-Dichloro-phenyl)-6-methyl-4H-3,1-benzoxazin-4-one
2-(2,6-Difluoro-phenyl)-6-methoxy-benzo[d][1,3]oxazin-4-one
2-(2-Fluoro-phenyl)-6-methoxy-benzo[d][1,3]oxazin-4-one
2-(2,6-Difluoro-phenyl)-7-trifluoromethyl-benzo[d][1,3]oxazin-4-one
6,7-Difluoro-2-(2-fluoro-phenyl)-benzo[d][1,3]oxazin-4-one
6,7-Difluoro-2-thiophen-2-yl-benzo[d][1,3]oxazin-4-one
6,7-Difluoro-2-furan-2-yl-benzo[d][1,3]oxazin-4-one
2-(2,6-Difluoro-phenyl)-4-oxo-4H-benzo[d][1,3]oxazine-5-carboxylic acid methyl ester
2-(2-Fluoro-phenyl)-4-oxo-4H-benzo[d][1,3]oxazine-5-carboxylic acid methyl ester
4-Oxo-2-thiophen-2-yl-4H-benzo[d][1,3]oxazine-5-carboxylic acid methyl ester
2-Furan-2-yl-4-oxo-4H-benzo[d][1,3]oxazine-5-carboxylic acid methyl ester
2-(2-Methoxy-phenyl)-6-nitro-benzo[d][1,3]oxazin-4-one
2-(2-Methoxy-phenyl)-5-methyl-benzo[d][1,3]oxazin-4-one
2-(2-Methoxy-phenyl)-5-nitro-benzo[d][1,3]oxazin-4-one
6-Nitro-2-(2-nitro-phenyl)-benzo[d][1,3]oxazin-4-one
6-Nitro-2-o-tolyl-benzo[d][1,3]oxazin-4-one
5-Nitro-2-(2-nitro-phenyl)-benzo[d][1,3]oxazin-4-one
5-Nitro-2-(2-nitro-phenyl)-benzo[d][1,3]oxazin-4-one
2-(2,3-Difluoro-phenyl)-6-nitro-benzo[d][1,3]oxazin-4-one
2-(2,3-Difluoro-phenyl)-5-methyl-benzo[d][1,3]oxazin-4-one
2-(2,3-Difluoro-phenyl)-5-nitro-benzo[d][1,3]oxazin-4-one
Acetic acid 2-(6-nitro-4-oxo-4H-benzo[d][1,3]oxazin-2-yl)-phenyl ester
Acetic acid 2-(5-methyl-4-oxo-4H-benzo[d][1,3]oxazin-2-yl)-phenyl ester
Acetic acid 2-(5-nitro-4-oxo-4H-benzo[d][1,3]oxazin-2-yl)-phenyl ester
2-(2,6-Difluoro-phenyl)-6-trifluoromethyl-benzo[d][1,3]oxazin-4-one
2-(2-Fluoro-phenyl)-6-trifluoromethyl-benzo[d][1,3]oxazin-4-one
2-Thiophen-2-yl-6-trifluoromethyl-benzo[d][1,3]oxazin-4-one
2-(2,6-Difluoro-phenyl)-5-trifluoromethyl-benzo[d][1,3]oxazin-4-one
2-(2-Fluoro-phenyl)-5-trifluoromethyl-benzo[d][1,3]oxazin-4-one
2-Thiophen-2-yl-5-trifluoromethyl-benzo[d][1,3]oxazin-4-one
2-(2,6-Difluoro-phenyl)-8-trifluoromethyl-benzo[d][1,3]oxazin-4-one
2-(2-Fluoro-phenyl)-8-trifluoromethyl-benzo[d][1,3]oxazin-4-one
2-Furan-2-yl-8-trifluoromethyl-benzo[d][1,3]oxazin-4-one
2-(2-Fluoro-phenyl )-4-oxo-4H-benzo[d][1,3]oxazine-5-carboxylic acid ethyl ester
2-(2,6-Difluoro-phenyl)-7-fluoro-benzo[d][1,3]oxazin-4-one
5-Nitro-2-(5-nitro-fu ran-2-yl)-benzo[d][1,3]oxazin-4-one 2-(2,3-Dichloro-phenyl)-6,7-difluoro-benzo[d][1,3]oxazin-4-one 6,7-Difluoro-2-(2-trifluoromethoxy-phenyl)-benzo[d][1,3]oxazin-4-one 2-(2,3-Difluoro-phenyl)-6,7-difluoro-benzo[d][1,3]oxazin-4-one 6,7-Difluoro-2-(2-methoxy-phenyl)-benzo[d][1,3]oxazin-4-one 2-(2,6-Difluoro-phenyl)-6-nitro-benzo[d][1,3]oxazin-4-one 6-Acetamido-(2,6-difluoro-phenyl)-benzo[d][1,3]oxazin-4-one 2-(2,6-Difluoro-phenyl)-5-methyl-benzo[d][1,3]oxazin-4-one 2-(2,6-Difluoro-phenyl)-7-nitro-benzo[d][1,3]oxazin-4-one 2-(2,6-Difluoro-phenyl)-5-nitro-benzo[d][1,3]oxazin-4-one 5-Chloro-2-(2,6-difluoro-phenyl)-benzo[d][1,3]oxazin-4-one 6-Amino-2-(2,6-difluoro-phenyl)-benzo[d][1,3]oxazin-4-one 2-(2,6-Difluoro-phenyl)-8-hydroxy-benzo[d][1,3]oxazin-4-one 5,8-Dichloro-2-(2,6-difluoro-phenyl)-benzo[d][1,3]oxazin-4-one 5-Amino-2-(2,6-difluoro-phenyl)-benzo[d][1,3]oxazin-4-one 2-(2,6-Difluoro-phenyl)-6,7-difluoro-benzo[d][1,3]oxazin-4-one 7-Amino-2-(2,6-difluoro-phenyl)-benzo[d][1,3]oxazin-4-one or pharmaceutical acceptable salts thereof.

12. A pharmaceutical composition comprising a therapeutically effective amount of the compound of claim 11, in combination with a pharmaceutically acceptable excipient and/or carrier.

13. The pharmaceutical composition of claim 12, which is administered orally.

* * * * *